(12) United States Patent
Jarrett et al.

(10) Patent No.: US 8,961,501 B2
(45) Date of Patent: Feb. 24, 2015

(54) METHOD FOR APPLYING FLOWABLE HYDROGELS TO A CORNEA

(75) Inventors: Peter Jarrett, Sudbury, MA (US); Rami El Hayek, Needham, MA (US); Michael Bassett, Pepperell, MA (US); James Biggins, Waltham, MA (US)

(73) Assignee: Incept, LLC, Bedford, MA (US)

( * ) Notice: Subject to any disclaimer, the term of this patent is extended or adjusted under 35 U.S.C. 154(b) by 752 days.

(21) Appl. No.: 12/884,466

(22) Filed: Sep. 17, 2010

(65) Prior Publication Data

US 2012/0071865 A1    Mar. 22, 2012

(51) Int. Cl.
| | | |
|---|---|---|
| A61B 18/18 | (2006.01) |
| A61F 2/00 | (2006.01) |
| A61K 9/00 | (2006.01) |
| A61K 9/06 | (2006.01) |
| A61K 47/34 | (2006.01) |

(52) U.S. Cl.
CPC ............... *A61K 9/0048* (2013.01); *A61K 9/06* (2013.01); *A61K 47/34* (2013.01)
USPC ............................................. 606/4; 424/427

(58) Field of Classification Search
USPC .............................................. 606/4; 424/427
See application file for complete search history.

(56) References Cited

U.S. PATENT DOCUMENTS

| | | |
|---|---|---|
| 703,101 A | 6/1902 | Ware |
| 3,158,183 A | 11/1964 | Brown et al. |
| 4,117,728 A | 10/1978 | Johnson |
| 4,341,218 A | 7/1982 | Ü |
| 4,641,653 A | 2/1987 | Rockey |
| 4,693,887 A | 9/1987 | Shah |
| 4,728,328 A | 3/1988 | Hughes et al. |
| 4,740,534 A | 4/1988 | Matsuda et al. |
| 4,741,872 A | 5/1988 | Deluca et al. |
| 4,760,131 A | 7/1988 | Sundsmo et al. |
| 4,803,075 A | 2/1989 | Wallace et al. |
| 4,826,945 A | 5/1989 | Cohn et al. |
| 4,938,763 A | 7/1990 | Dunn et al. |
| 4,952,581 A | 8/1990 | Bio et al. |

(Continued)

FOREIGN PATENT DOCUMENTS

| | | |
|---|---|---|
| EP | 1 704 878 A2 | 9/2006 |
| EP | 1 967 220 A2 | 9/2008 |

(Continued)

OTHER PUBLICATIONS

Confluent Surgical Duraseal packaging, Ref. 10-5005, LCN-2005-101, Rev. 02 (2 pages).

(Continued)

*Primary Examiner* — Lynsey Crandall
*Assistant Examiner* — Sebastian X Lukjan
(74) *Attorney, Agent, or Firm* — Dardi & Herbert, PLLC; Curtis B. Herbert

(57) ABSTRACT

Materials and methods of treating an eye with a hydrogel formed on the eye. Embodiments are provided that include post-keratectomy bandages. A method of treating a patient by application of a hydrogel bandage to a cornea by providing a first hydrogel precursor in a dry form immobilized in a first deposit at a first location in a well, providing a second hydrogel precursor in a dry form immobilized in a second deposit at a second location in the well, mixing the deposits together to form a mixture, and transferring at least some of the mixture to the cornea, with the mixture forming a covalently crosslinked hydrogel on the cornea.

11 Claims, 8 Drawing Sheets

(56) References Cited

U.S. PATENT DOCUMENTS

| | | |
|---|---|---|
| 4,979,959 A | 12/1990 | Guire |
| 5,041,292 A | 8/1991 | Feijen |
| 5,100,992 A | 3/1992 | Cohn et al. |
| 5,122,614 A | 6/1992 | Zalipsky |
| 5,147,647 A | 9/1992 | Darougar et al. |
| 5,154,702 A | 10/1992 | Foyil |
| 5,160,745 A | 11/1992 | Deluca et al. |
| 5,162,430 A | 11/1992 | Rhee et al. |
| 5,227,372 A | 7/1993 | Folkman |
| 5,266,325 A | 11/1993 | Kuzma et al. |
| 5,272,012 A | 12/1993 | Opolski |
| 5,278,202 A | 1/1994 | Dunn et al. |
| 5,286,257 A | 2/1994 | Fischer |
| 5,296,228 A | 3/1994 | Chang et al. |
| 5,304,595 A | 4/1994 | Rhee et al. |
| 5,306,500 A | 4/1994 | Rhee et al. |
| 5,322,691 A | 6/1994 | Darougar et al. |
| 5,324,775 A | 6/1994 | Rhee et al. |
| 5,368,563 A | 11/1994 | Lonneman et al. |
| 5,380,536 A | 1/1995 | Hubbell et al. |
| 5,395,618 A | 3/1995 | Darougar et al. |
| 5,410,016 A | 4/1995 | Hubbell et al. |
| 5,446,090 A | 8/1995 | Harris |
| 5,446,091 A | 8/1995 | Rhee et al. |
| 5,462,990 A | 10/1995 | Hubbell et al. |
| 5,464,396 A | 11/1995 | Barta et al. |
| 5,466,680 A | 11/1995 | Rudy |
| 5,480,914 A | 1/1996 | Meadows |
| 5,510,418 A | 4/1996 | Rhee et al. |
| 5,514,379 A | 5/1996 | Weissleder et al. |
| 5,527,856 A | 6/1996 | Rhee et al. |
| 5,529,914 A | 6/1996 | Hubbell et al. |
| 5,530,528 A | 6/1996 | Houki et al. |
| 5,534,024 A | 7/1996 | Rogers et al. |
| 5,543,441 A | 8/1996 | Rhee et al. |
| 5,550,187 A | 8/1996 | Rhee et al. |
| 5,550,188 A | 8/1996 | Rhee et al. |
| 5,565,215 A | 10/1996 | Gref et al. |
| 5,565,519 A | 10/1996 | Rhee et al. |
| 5,567,435 A | 10/1996 | Hubbell et al. |
| 5,567,440 A | 10/1996 | Hubbell et al. |
| 5,573,934 A | 11/1996 | Hubbell et al. |
| 5,578,638 A | 11/1996 | Brazzell et al. |
| 5,583,114 A | 12/1996 | Barrows et al. |
| 5,587,175 A | 12/1996 | Viegas et al. |
| 5,603,991 A | 2/1997 | Kupiecki et al. |
| 5,618,563 A | 4/1997 | Berde et al. |
| 5,626,863 A | 5/1997 | Hubbell et al. |
| 5,627,233 A | 5/1997 | Hubbell et al. |
| 5,650,173 A | 7/1997 | Ramstack et al. |
| 5,660,849 A | 8/1997 | Polson et al. |
| 5,662,712 A | 9/1997 | Pathak et al. |
| 5,665,117 A | 9/1997 | Rhodes |
| 5,665,840 A | 9/1997 | Pohlmann et al. |
| 5,690,671 A | 11/1997 | McGurk et al. |
| 5,693,088 A | 12/1997 | Lazarus |
| 5,705,194 A | 1/1998 | Wong et al. |
| 5,714,159 A | 2/1998 | Shalaby |
| 5,717,614 A | 2/1998 | Shah et al. |
| 5,731,005 A | 3/1998 | Ottoboni et al. |
| 5,741,323 A | 4/1998 | Pathak et al. |
| 5,744,545 A | 4/1998 | Rhee et al. |
| 5,752,974 A | 5/1998 | Rhee et al. |
| 5,769,882 A | 6/1998 | Fogarty et al. |
| 5,776,445 A | 7/1998 | Cohen et al. |
| 5,800,373 A | 9/1998 | Melanson et al. |
| 5,801,033 A | 9/1998 | Hubbell et al. |
| 5,820,882 A | 10/1998 | Hubbell et al. |
| 5,823,198 A | 10/1998 | Jones et al. |
| 5,824,037 A | 10/1998 | Fogarty et al. |
| 5,834,274 A | 11/1998 | Hubbell et al. |
| 5,837,226 A | 11/1998 | Jungherr et al. |
| 5,843,160 A | 12/1998 | Rhodes |
| 5,843,743 A | 12/1998 | Hubbell et al. |
| 5,844,016 A | 12/1998 | Sawhney et al. |
| 5,849,035 A | 12/1998 | Pathak et al. |
| 5,849,839 A | 12/1998 | Hubbell et al. |
| 5,851,508 A | 12/1998 | Greff et al. |
| 5,858,746 A | 1/1999 | Hubbell et al. |
| 5,874,500 A | 2/1999 | Rhee et al. |
| 5,876,448 A | 3/1999 | Thompson et al. |
| 5,879,688 A | 3/1999 | Coury et al. |
| 5,888,493 A | 3/1999 | Sawaya |
| 5,932,462 A | 8/1999 | Harris et al. |
| 5,936,035 A | 8/1999 | Rhee et al. |
| 5,962,023 A | 10/1999 | Jamiolkowski et al. |
| 5,981,607 A | 11/1999 | Ding et al. |
| 5,986,043 A | 11/1999 | Hubbell et al. |
| 5,989,579 A | 11/1999 | Darougar et al. |
| 5,994,750 A | 11/1999 | Yagi et al. |
| 6,051,648 A | 4/2000 | Rhee et al. |
| 6,060,582 A | 5/2000 | Hubbell et al. |
| 6,066,564 A | 5/2000 | Li et al. |
| 6,071,875 A | 6/2000 | Clark et al. |
| 6,083,524 A | 7/2000 | Sawhney et al. |
| 6,110,198 A | 8/2000 | Fogarty et al. |
| 6,110,484 A | 8/2000 | Sierra |
| 6,121,341 A | 9/2000 | Sawhney et al. |
| 6,123,667 A | 9/2000 | Poff et al. |
| 6,132,986 A | 10/2000 | Pathak et al. |
| 6,149,614 A | 11/2000 | Dunshee et al. |
| 6,149,931 A | 11/2000 | Schwartz et al. |
| 6,152,943 A | 11/2000 | Sawhney |
| 6,153,211 A | 11/2000 | Hubbell et al. |
| 6,154,671 A | 11/2000 | Parel et al. |
| 6,156,345 A | 12/2000 | Chudzik et al. |
| 6,156,531 A | 12/2000 | Pathak et al. |
| 6,162,241 A | 12/2000 | Coury et al. |
| 6,165,201 A | 12/2000 | Sawhney et al. |
| 6,165,489 A | 12/2000 | Berg et al. |
| 6,166,130 A | 12/2000 | Rhee et al. |
| 6,168,592 B1 | 1/2001 | Kupiecki et al. |
| 6,171,600 B1 | 1/2001 | Dahms |
| 6,176,871 B1 | 1/2001 | Pathak et al. |
| 6,177,095 B1 | 1/2001 | Sawhney et al. |
| 6,177,514 B1 | 1/2001 | Pathak et al. |
| 6,179,862 B1 | 1/2001 | Sawhney |
| 6,190,402 B1 | 2/2001 | Horton et al. |
| 6,193,745 B1 | 2/2001 | Fogarty et al. |
| 6,196,230 B1 | 3/2001 | Hall et al. |
| 6,201,065 B1 | 3/2001 | Pathak et al. |
| 6,214,966 B1 | 4/2001 | Harris |
| 6,217,896 B1 | 4/2001 | Benjamin |
| 6,220,246 B1 | 4/2001 | Chandler et al. |
| 6,231,892 B1 | 5/2001 | Hubbell et al. |
| 6,242,442 B1 | 6/2001 | Dean et al. |
| 6,258,870 B1 | 7/2001 | Hubbell et al. |
| 6,261,305 B1 | 7/2001 | Marotta et al. |
| 6,261,544 B1 | 7/2001 | Coury et al. |
| 6,264,971 B1 | 7/2001 | Darougar et al. |
| 6,277,394 B1 | 8/2001 | Sierra |
| 6,283,991 B1 | 9/2001 | Cox et al. |
| 6,296,603 B1 | 10/2001 | Turnlund et al. |
| 6,297,240 B1 | 10/2001 | Embleton |
| 6,299,597 B1 | 10/2001 | Buscemi et al. |
| 6,306,922 B1 | 10/2001 | Hubbell et al. |
| 6,312,462 B1 | 11/2001 | McDermott et al. |
| 6,312,463 B1 | 11/2001 | Rourke et al. |
| 6,312,725 B1 | 11/2001 | Wallace et al. |
| 6,316,441 B1 | 11/2001 | Dean et al. |
| 6,319,240 B1 | 11/2001 | Beck |
| 6,322,593 B1 | 11/2001 | Pathak et al. |
| 6,331,184 B1 | 12/2001 | Abrams |
| 6,334,869 B1 | 1/2002 | Leonhardt et al. |
| 6,335,335 B2 | 1/2002 | Higashiyama et al. |
| 6,371,975 B2 | 4/2002 | Cruise et al. |
| 6,379,373 B1 | 4/2002 | Sawhney et al. |
| 6,387,977 B1 | 5/2002 | Sawhney et al. |
| 6,409,757 B1 | 6/2002 | Trout, III et al. |
| 6,410,045 B1 | 6/2002 | Schultz et al. |
| 6,410,645 B1 | 6/2002 | Pathak et al. |
| 6,413,539 B1 | 7/2002 | Shalaby |
| 6,416,740 B1 | 7/2002 | Unger |
| 6,458,147 B1 | 10/2002 | Cruise et al. |

(56) References Cited

U.S. PATENT DOCUMENTS

| | | |
|---|---|---|
| 6,458,889 B1 | 10/2002 | Trollsas et al. |
| 6,463,317 B1 | 10/2002 | Kucharczyk et al. |
| 6,465,001 B1 | 10/2002 | Hubbell et al. |
| 6,479,079 B1 | 11/2002 | Pathak et al. |
| 6,495,127 B1 | 12/2002 | Wallace et al. |
| 6,506,204 B2 | 1/2003 | Mazzocchi |
| 6,514,534 B1 | 2/2003 | Sawhney |
| 6,528,107 B2 | 3/2003 | Chinn et al. |
| 6,534,591 B2 | 3/2003 | Rhee et al. |
| 6,539,251 B2 | 3/2003 | Beck et al. |
| 6,544,276 B1 | 4/2003 | Azizi |
| 6,566,406 B1 | 5/2003 | Pathak et al. |
| 6,579,519 B2 | 6/2003 | Maitra et al. |
| 6,592,614 B2 | 7/2003 | Lenker et al. |
| 6,596,471 B2 | 7/2003 | Pathak et al. |
| 6,602,975 B2 | 8/2003 | Hubbell et al. |
| 6,605,294 B2 | 8/2003 | Sawhney |
| 6,610,033 B1 | 8/2003 | Melanson et al. |
| 6,613,037 B2 | 9/2003 | Khosravi et al. |
| 6,624,245 B2 | 9/2003 | Wallace et al. |
| 6,632,446 B1 | 10/2003 | Hubbell et al. |
| 6,632,457 B1 | 10/2003 | Sawhney |
| 6,639,014 B2 | 10/2003 | Pathak et al. |
| 6,656,200 B2 | 12/2003 | Li et al. |
| 6,656,214 B1 | 12/2003 | Fogarty et al. |
| 6,663,607 B2 | 12/2003 | Slikeu et al. |
| 6,663,667 B2 | 12/2003 | Dehdashtian et al. |
| 6,673,093 B1 | 1/2004 | Sawhney |
| 6,689,148 B2 | 2/2004 | Sawhney et al. |
| 6,703,047 B2 | 3/2004 | Sawhney et al. |
| 6,709,668 B2 | 3/2004 | Won et al. |
| 6,710,126 B1 | 3/2004 | Hirt et al. |
| 6,711,879 B2 | 3/2004 | Korteweg et al. |
| 6,730,119 B1 | 5/2004 | Smalling |
| 6,747,090 B2 | 6/2004 | DeGroot et al. |
| 6,777,000 B2 | 8/2004 | Ni et al. |
| 6,818,018 B1 | 11/2004 | Sawhney |
| 6,827,735 B2 | 12/2004 | Greenberg |
| 6,833,408 B2 | 12/2004 | Sehl et al. |
| 6,843,803 B2 | 1/2005 | Ryan et al. |
| 6,861,065 B2 | 3/2005 | Hodd et al. |
| 6,887,974 B2 | 5/2005 | Pathak |
| 6,905,700 B2 | 6/2005 | Won et al. |
| 6,911,227 B2 | 6/2005 | Hubbell et al. |
| 6,911,496 B2 | 6/2005 | Rhee et al. |
| 6,916,857 B2 | 7/2005 | Won et al. |
| 6,918,926 B2 | 7/2005 | Letort |
| 6,923,986 B2 | 8/2005 | Pathak et al. |
| 6,936,005 B2 | 8/2005 | Poff et al. |
| 6,958,212 B1 | 10/2005 | Hubbell et al. |
| 6,960,227 B2 | 11/2005 | Jones et al. |
| 6,962,979 B1 | 11/2005 | Rhee |
| 7,009,034 B2 | 3/2006 | Pathak et al. |
| 7,025,990 B2 | 4/2006 | Sawhney |
| 7,057,019 B2 | 6/2006 | Pathak |
| 7,060,297 B2 | 6/2006 | Karakelle et al. |
| 7,129,210 B2 | 10/2006 | Lowinger et al. |
| 7,141,248 B2 | 11/2006 | Hodd et al. |
| 7,153,519 B2 | 12/2006 | Hubbell et al. |
| 7,211,651 B2 | 5/2007 | Pathak |
| 7,220,270 B2 | 5/2007 | Sawhney et al. |
| RE39,713 E | 7/2007 | Sawhney et al. |
| 7,238,364 B2 | 7/2007 | Sawhney et al. |
| 7,290,573 B2 | 11/2007 | Py et al. |
| 7,589,057 B2 | 9/2009 | Chang et al. |
| 7,862,538 B2 | 1/2011 | Sawhney et al. |
| 2002/0026176 A1 | 2/2002 | Varner et al. |
| 2002/0026217 A1 | 2/2002 | Baker et al. |
| 2002/0045848 A1 | 4/2002 | Jaafar et al. |
| 2002/0052643 A1 | 5/2002 | Wholey et al. |
| 2002/0064513 A1 | 5/2002 | Maitra et al. |
| 2002/0071874 A1 | 6/2002 | Olejnik et al. |
| 2002/0112981 A1* | 8/2002 | Cooper et al. ............ 206/438 |
| 2002/0114778 A1 | 8/2002 | Xia et al. |
| 2002/0119941 A1 | 8/2002 | Ni et al. |
| 2002/0197300 A1 | 12/2002 | Schultz et al. |
| 2003/0012734 A1 | 1/2003 | Pathak et al. |
| 2003/0014075 A1 | 1/2003 | Rosenbluth et al. |
| 2003/0017199 A1 | 1/2003 | Woodward et al. |
| 2003/0051735 A1 | 3/2003 | Pavcnik et al. |
| 2003/0130725 A1 | 7/2003 | DePalma et al. |
| 2003/0135269 A1 | 7/2003 | Swanstrom |
| 2003/0147849 A1 | 8/2003 | Warne et al. |
| 2003/0175324 A1 | 9/2003 | Robinson et al. |
| 2003/0185892 A1 | 10/2003 | Bell et al. |
| 2003/0191426 A1 | 10/2003 | Lerner et al. |
| 2003/0204242 A1 | 10/2003 | Zarins et al. |
| 2003/0204249 A1 | 10/2003 | Letort |
| 2003/0216802 A1 | 11/2003 | Chobotov et al. |
| 2004/0009205 A1 | 1/2004 | Sawhney |
| 2004/0016997 A1 | 1/2004 | Ushio |
| 2004/0037889 A1 | 2/2004 | Richeal et al. |
| 2004/0044358 A1 | 3/2004 | Khosravi et al. |
| 2004/0082989 A1 | 4/2004 | Cook et al. |
| 2004/0086479 A1 | 5/2004 | Grinstaff et al. |
| 2004/0098096 A1 | 5/2004 | Eton |
| 2004/0131582 A1 | 7/2004 | Grinstaff et al. |
| 2004/0204755 A1 | 10/2004 | Robin |
| 2004/0230183 A1 | 11/2004 | Breegi et al. |
| 2005/0004660 A1 | 1/2005 | Rosenbluth et al. |
| 2005/0028484 A1 | 2/2005 | Littlewood |
| 2005/0043220 A1 | 2/2005 | Guyer et al. |
| 2005/0065592 A1 | 3/2005 | Holzer |
| 2005/0080445 A1 | 4/2005 | Sawhney et al. |
| 2005/0169882 A1 | 8/2005 | Lowe et al. |
| 2005/0209555 A1 | 9/2005 | Middleton et al. |
| 2005/0232872 A1 | 10/2005 | Deaver et al. |
| 2005/0244464 A1 | 11/2005 | Hughes |
| 2005/0277864 A1 | 12/2005 | Haffner et al. |
| 2006/0002963 A1 | 1/2006 | Rabinovich-Guilatt et al. |
| 2006/0013859 A1 | 1/2006 | Yamada et al. |
| 2006/0025853 A1 | 2/2006 | Evans et al. |
| 2006/0039479 A1 | 2/2006 | Francois et al. |
| 2006/0039979 A1 | 2/2006 | Yamada et al. |
| 2006/0079599 A1 | 4/2006 | Arthur |
| 2006/0100288 A1 | 5/2006 | Bague et al. |
| 2006/0147409 A1 | 7/2006 | Pathak et al. |
| 2006/0177481 A1 | 8/2006 | Sawhney |
| 2006/0182771 A1 | 8/2006 | Dor et al. |
| 2006/0182781 A1 | 8/2006 | Hughes et al. |
| 2006/0193899 A1 | 8/2006 | Sawhney |
| 2006/0258698 A1* | 11/2006 | Mudumba et al. ............ 514/291 |
| 2006/0275336 A1 | 12/2006 | Du Plessis |
| 2006/0286173 A1 | 12/2006 | Yamada et al. |
| 2007/0168025 A1 | 7/2007 | Darougar et al. |
| 2007/0195261 A1 | 8/2007 | Vogt et al. |
| 2007/0197776 A1 | 8/2007 | Pathak |
| 2007/0224246 A1 | 9/2007 | Hughes et al. |
| 2007/0231366 A1 | 10/2007 | Sawhney et al. |
| 2007/0233240 A1 | 10/2007 | Frank et al. |
| 2007/0248567 A1 | 10/2007 | Pathak et al. |
| 2007/0282366 A1 | 12/2007 | Khosravi et al. |
| 2008/0038317 A1 | 2/2008 | Chang et al. |
| 2008/0114092 A1 | 5/2008 | Sawhney |
| 2008/0187568 A1 | 8/2008 | Sawhney |
| 2008/0220047 A1 | 9/2008 | Sawhney et al. |
| 2008/0268020 A1 | 10/2008 | Philips et al. |
| 2009/0017097 A1* | 1/2009 | Sawhney et al. ............ 424/427 |
| 2009/0215923 A1 | 8/2009 | Carnahan et al. |
| 2010/0104654 A1 | 4/2010 | Robinson et al. |
| 2010/0158980 A1 | 6/2010 | Kopczynski et al. |
| 2010/0209478 A1 | 8/2010 | Sawhney et al. |

FOREIGN PATENT DOCUMENTS

| | | |
|---|---|---|
| WO | 97/19973 A1 | 6/1997 |
| WO | 98/12274 A1 | 3/1998 |
| WO | 98/35631 A1 | 8/1998 |
| WO | 00/09199 A1 | 2/2000 |
| WO | 00/51522 A1 | 9/2000 |
| WO | 01/21108 A1 | 3/2001 |
| WO | 01/66038 A2 | 9/2001 |
| WO | 02/102282 A1 | 12/2002 |
| WO | 2004/028404 A2 | 4/2004 |

(56) References Cited

FOREIGN PATENT DOCUMENTS

| WO | 2006/026325 | A2 | 3/2006 |
|----|-------------|----|--------|
| WO | 2006/031358 | A2 | 3/2006 |
| WO | 2006/031388 | A2 | 3/2006 |
| WO | 2006/096586 | A1 | 9/2006 |
| WO | 2007/001926 | A2 | 1/2007 |
| WO | 2007/005249 | A2 | 1/2007 |

OTHER PUBLICATIONS

CoSeal Surgical Sealant, 0700169 Rev. 2 Rev. Date Mar. 2006 (2 pages).

Dunn et al., "Evaluation of the SprayGel adhesion barrier in the rat cecum abrasion and rabbit uterine horn adhesion models", Fertility and Sterility, 75(2): 411-416 (Feb. 2001).

Internet Archive, Search results for (http://chemistry2.csudh.edu/rpedarvis/AmAcSeqSyn.html., Accessed Mar. 23, 2009 (1 page).

Lou et al., "Drug release characteristics of phase separation pHEMA sponge materials", Biomaterials, 25:5071-5080 (2004).

Neises et al., "Esterification of Carboxylic Acids with Dicyclohexylcarbodiimide/4-Dimethylaminopyridime: tert-Butyl Ethyl Fumarate", Organic Syntheses, Coll. vol. 7, p. 93 (1990) ; vol. 63, p. 183 (1985), see http://www.orgsyn.org/orgsyn/orgsyn/prepContent.asp?prep=cv7p0093 (4 pages).

Peptide Sequencing and Synthesis "Chemistry 240 Summer 2001.", May 8, 2003 (as of Internet Archive) see http://chemistry2csudh.edu/rpendarvis/Am/AcSeqSyn.html (9 pages).

Srividya et al., "Sustained Ophthalmic Delivery of Ofloxacin from a pH Triggered In Situ Gelling System", Journal of Controlled Release, 73:205-211 (2001).

* cited by examiner

METHOD FOR APPLYING FLOWABLE HYDROGELS TO A CORNEA

TECHNICAL FIELD

The technical field relates to formation of hydrogels on an ocular surface for treatment of an eye, and includes particular methods of applying the hydrogels as well as particular compositions of the same.

BACKGROUND

A wound on the surface of the eye caused by trauma or surgery can often be painful. Brushing of the eyelid against the eye can aggravate pain caused by the damage. The arts of applying a bandage between the eye and the eyelid, however, have generally not advanced to the point where such bandages can be routinely used.

SUMMARY OF THE INVENTION

Disclosed herein are hydrogel bandages for placement on an eye. The hydrogels may be formed directly on the eye from precursor materials that react with each other to form the hydrogel on the eye. The bandage adheres directly to the eye to minimize discomfort and complications that could result from movement of the bandage around the eye. The hydrogel can be made with an unexpected property: displacement from the eye by cell in-migration. The cells are unable to grow over or under the hydrogel. The hydrogel degrades and is displaced from its outside edges inwardly by epithelial cells. The interplay between the changing mechanical strength of the hydrogel and the activity of the epithelial cells are approximately matched. As a result, the wound edges are healed as the hydrogel withdraws from the wound, to thereby provide continuous coverage of the wound. These and other embodiments are set forth herein.

As illustrated in FIG. 1, panel (a) depicts a corneal surface 40 with a layer of epithelial cells 42 interrupted by a de-epithelialized zone 44. Although this zone is shallow, it is possible to apply precursor solutions only within the zone. As at panel (b), a volume 50 is applied to zone 44. The volume 50 is spread out with a brush, delivery surface, mixing rod, or other means and cross-links to form a hydrogel that has a height 52 close to the epithelial cell layer thickness. Height 52 may decrease over time as eyelids brush the gel, as at panel (c), with the hydrogel nonetheless remaining adherent. Migrating cells 56 subsequently migrate into the de-epithelialized zone, panels d and e, displacing the hydrogel, which becomes decreased in projected surface area, 54. Disappearance of the hydrogel progresses from outer edges of the zone to the center of the zone, with migrating epithelial cells 56 being continuously adjacent the hydrogel without being substantially under the hydrogel. The hydrogel may not be displaced symmetrically but is displaced progressively from its outer edges inwardly. Surface erosion of the gel may also occur. The de-epithelialized zone 44 eventually becomes re-epithelialized, panel f. Hydrogels and particular delivery systems and techniques for using this unexpected property are disclosed herein.

An alternative masking-based approach is illustrated at FIGS. 6A and 6B.

DETAILED DESCRIPTION OF PREFERRED EMBODIMENTS OF THE INVENTION

Figure 1:
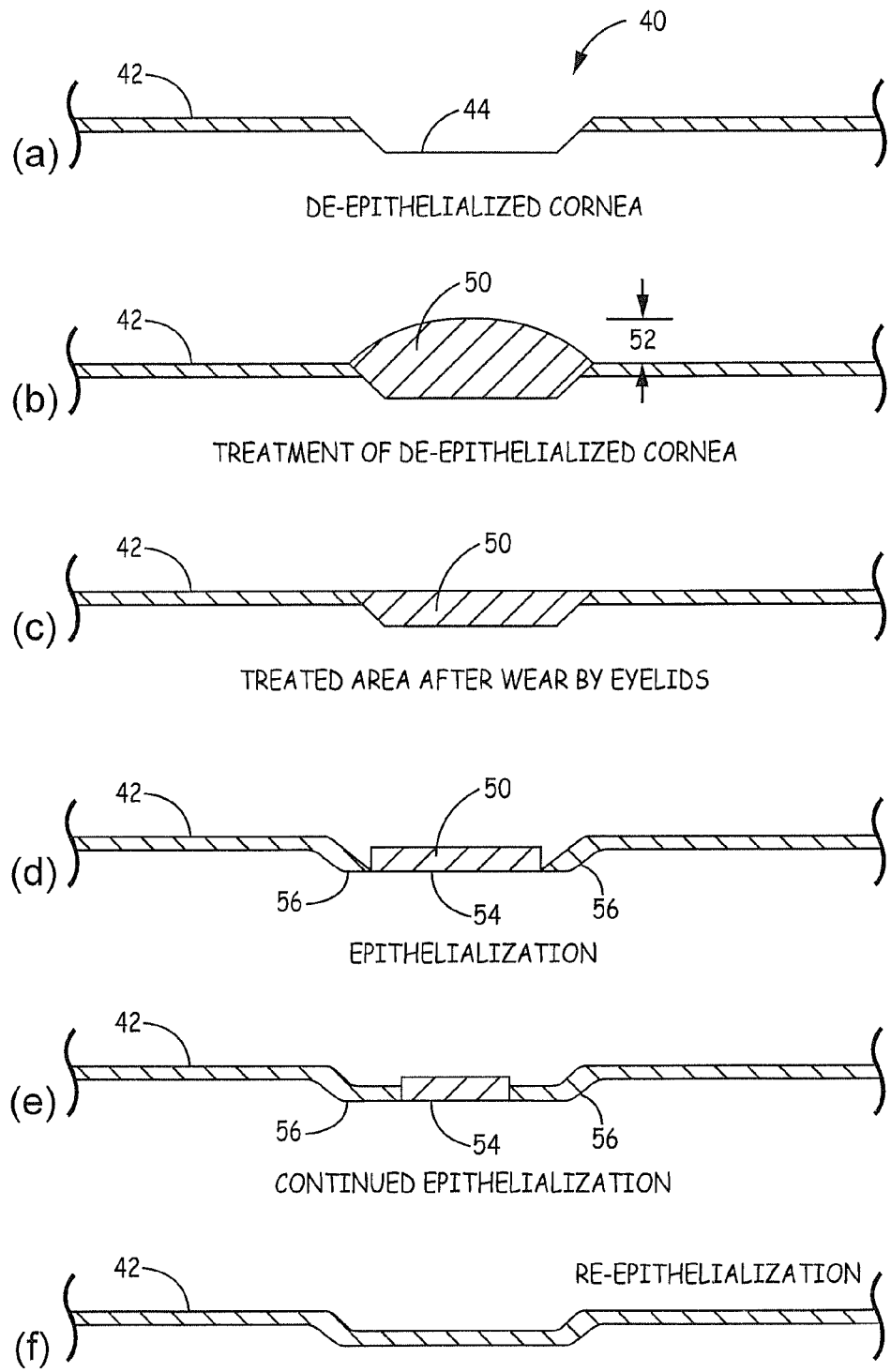
FIG. 1 is an illustration of cell-driven hydrogel degradation.

Hydrogel bandages may be placed on an eye following surgery or trauma to the cornea. The hydrogel adheres directly to the eye and reduces pain. The hydrogel can be made to degrade at a rate proportional to epithelial cell migration into the wound area (FIG. 1). Without being bound to a particular theory of operation, it is believed that the hydrogel allows cells to push its edges up and is weak and brittle enough to then be flaked-off by the eyelid. At the same time, the hydrogel otherwise has the mechanical strength needed to resist movement and displacement by the eyelid. These embodiments were observed to not otherwise allow cells to invade the area under the hydrogel or to allow cells to migrate over the hydrogel surface. Some hydrogels with unsuitable properties were observed to create a jumble of epithelial cells at the hydrogel edge so that there was no cell-driven dehiscence of the hydrogel from the eye. Another theory of operation, that is likewise not to be binding, is that nerve endings on the surface of the eye are most sensitive in the few days after the injury so that temporary coverage of the injured area that reduces or eliminates pain if the area is protected from mechanical forces, and especially eyelid movement.

One application is for treatment of an eye after surface ablation from vision correction surgical techniques such as photorefractive keratectomy (PRK) and a modified laser-assisted in situ keratomileusis (LASIK) known as epi-LASIK. These procedures involve creation of a de-epithelialized zone on the cornea. The zone is actually a depression on the eye surface, albeit a very shallow one measured in tens of microns, typically ranging from about 10 to about 200 microns. Since it has been discovered that hydrogels can be made with a range of structural properties that provide for cell-driven dehiscence (unbinding from the eye surface), it can be desirable to place the hydrogel only in the de-epithelialized zone. Such placement, however, requires new approaches to bandage placement.

One such approach is to paint or dab a flowable solution onto the surface and to let it flow, or spread it around, until it covers the zone. The volume of the solution may be controlled so that it does not spill substantially out of the zone and is thus retained substantially inside the zone so that it does not substantially overlap outside of the zone. Experimentation has shown that some spill-over can be tolerated with suitable materials since the excess material quickly flakes off. The term substantially, in this context, means that there is an overlap of less than about 2 mm outside of the zone, i.e., that the material is retained within 2 mm of the margin of the zone. The material may be said to be substantially only in the zone. Similarly, the amount of overlap may be specified, with the material being no more than about 1, about 2, or about 3 mm from the margin.

Also, control of the thickness of the resultant hydrogel can assist in the procedure if the hydrogel's height relative to the area outside the zone is kept to a minimum, e.g., less than about 200 μm; artisans will immediately appreciate that all the ranges and values within the explicitly stated range are contemplated, e.g., from about 10 to about 100 μm or less than 50 or within 1 to 50 μm of the top of the zone (including heights above or below the top of the zone). Control of the height can reduce the mechanical force of the eyelid moving across the eye so that displacement and movement are reduced. The solution must also have a desirable pH, since pH that is too basic is believed to have adverse effects, with a pH of about 6 to about 8 being preferred. The solution must also gel within a range of time that allows for the solution to be applied and spread as needed without undue opportunity to flow away or be accidentally moved in application. These processes are in contrast to conventional approaches of providing a material that generally covers the wound and areas around the wound.

Achieving the embodiments with cell-driven dehiscence of the hydrogel was unexpected. These embodiments reflect a balance of hydrogel strength, brittleness, ductility, adhesivity, degradation rates, distance between crosslinks, solids content, resistance to cellular attachment, pH at the time of application, flowability in placement, time to gelation, and shrinkage. These factors are often in tension with each other. For instance the material needs strength and ductility to stay in place over time but also must be brittle and weak enough to respond to cellular activity. The distance between crosslinks should be small enough to resist cellular migration but not such that the strength is unduly increased, or that passage of low molecular weight molecules such as drugs is impeded. The degradation rate must be fast enough for the hydrogel to spontaneously disappear but not too fast so that the hydrogel is gone before cells can re-cover the de-epithelialized zone.

Described herein is a material for an ocular bandage for corneal surface ablation that is a bioabsorbable, highly biocompatible corneal bandage that is applied as a thin liquid coating. This liquid may be painted onto the injured cornea and quickly transform into a tightly adherent hydrogel bandage that is optically transparent, providing a custom fit bandage for each corneal surface. Such bandages reduce or eliminate the pain and potentially improve vision during the healing period. The period of greatest pain has been reported to be up to 2 days, and re-establishment of the epithelium generally occurs within one week.

Creation of a degradable bandage presents some difficulty with the desire for the bandage to cover the wound but simultaneously not to interfere with healing. Herein are described hydrogels with a persistence of 2-20 days. A preferred range is about 2-6 days; a minimum of about 2 days persistence to protect the wound during the most painful period, while having the material substantially gone from the site at about 4 days to about 6 days will minimize any delay of healing. Artisans will immediately appreciate that all the ranges and values within the explicitly stated ranges are contemplated.

Photorefractive keratectomy (PRK) is a laser vision correction procedure for the treatment of myopia (nearsightedness), astigmatism, and hyperopia (farsightedness), with the intent to either eliminate or reduce the need for corrective eyewear. Patients treated with PRK are less likely to develop complications after surgery than another laser eye surgery procedure called laser-assisted in situ keratomileusis (LASIK). Unlike LASIK, the PRK procedure does not create a corneal flap, which can weaken the cornea, and is thus free from flap related medical complications. LASIK flap complications can include corneal ectasia, in-growth of epithelial cells, folds within the flap and a long term risk of flap dislocation. In addition, flap incisions can result in severed nerves that control tear production, leading to a chronic condition called "dry eye". In PRK, the surface of the cornea is directly ablated without making a corneal flap, thereby making it a more robust surgical procedure for correcting vision. The PRK procedure might require a slightly longer healing time but has less risk of complication than LASIK. The PRK procedure, however, causes pain believed to be resulting from the exposed nerve endings that are laid bare and a period (days) of poor vision until the epithelial tissue has healed. These two drawbacks have limited the popularity of this procedure.

Epi-LASIK is a modification of LASIK in which the flap created is limited to the epithelium of the cornea by use of a specialized microkeratome. The thinner flap is considered advantageous because the Bowman's membrane is not disturbed except in the area where the laser ablation is administered. In many cases the epithelial layer is discarded, making Epi-LASIK similar to PRK, with the major difference being the method of epithelium removal.

Example 1 describes a hydrogel that, while useful in other ocular healing contexts, failed to be effective for post-PRK bandaging. This hydrogel, described in detail in the Example, had a formulation of 8 arm 15K SG PEG and trilysine. This gel was tested over a range of solids content and gelation times. The swelling of the hydrogel varied considerably and passed through a minimum while solids content and gelation times were decreased and increased, respectively. In vivo, the gel persisted over 15 days and, at that point, it seemed to be degraded such that it was partially de-adhered and reshaped by movement of the eyelid.

Example 2 describes another hydrogel that, while useful in other ocular healing contexts, also failed to be effective for post-PRK bandaging. The formulation of Example 1 was adjusted by changing the pH of the reaction solution upon dilution by adding the sodium phosphate dibasic and sodium tetraborate decahydrate to the diluent instead of dried deposits. Unexpectedly, the persistence time of the gel in vivo was not greatly changed even though lower solid content formulations were tested.

Figure 2:
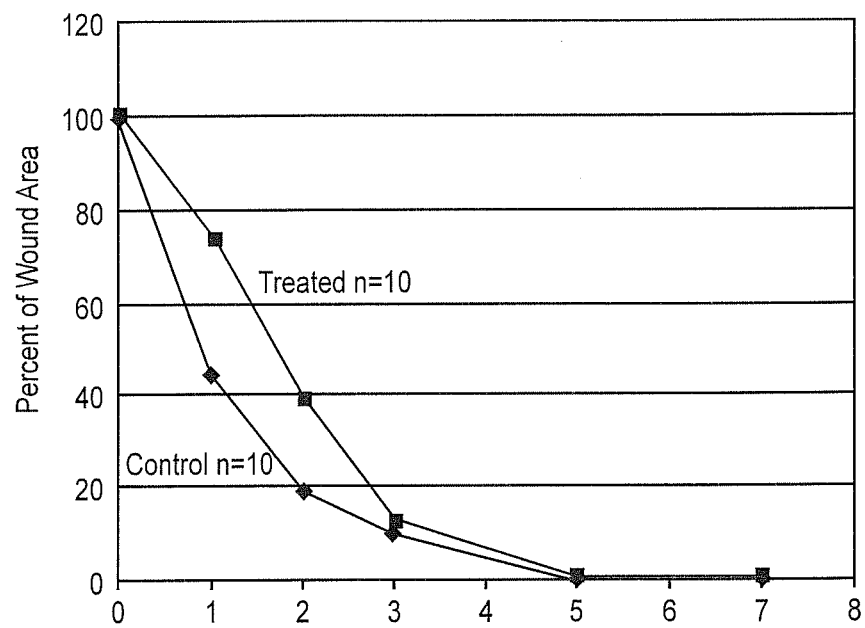
FIG. 2 is a plot of healing in both control and hydrogel-treated eyes.
Figure 3:
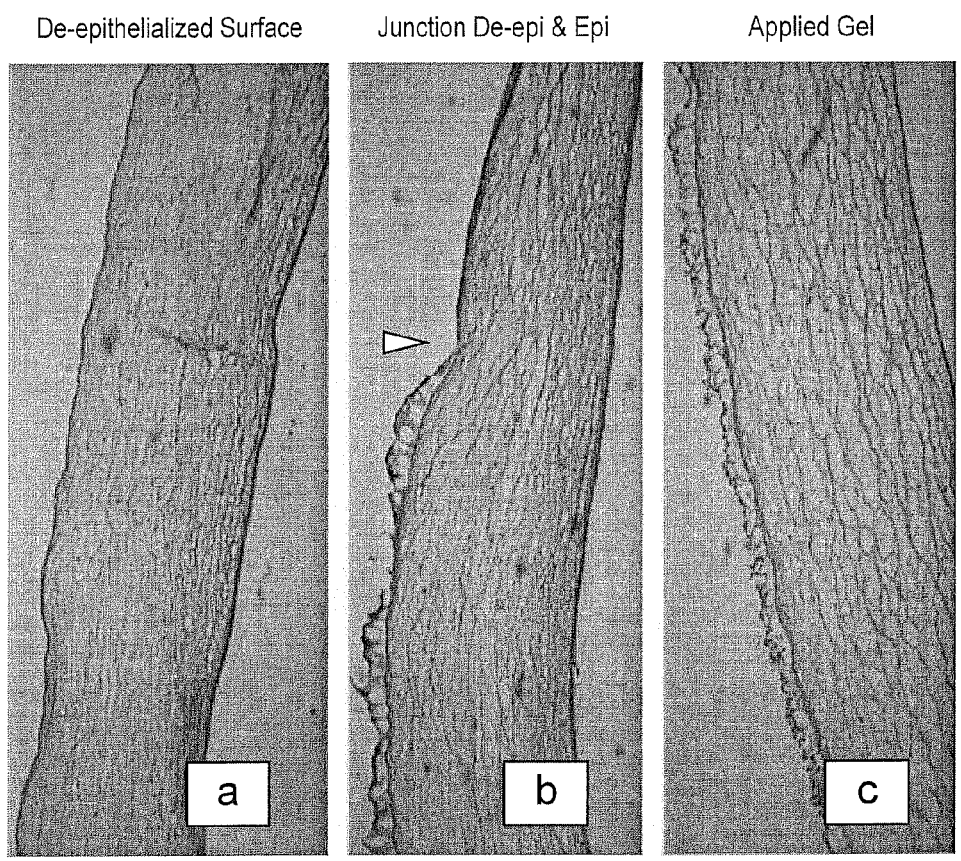
FIG. 3 is a photomicrograph of histology sections showing (a) a de-epithelialized corneal surface, (b) cells driving dehiscence of the hydrogel on the corneal surface as indicated by the arrowhead, and (c) a hydrogel covering of the de-epithelialized zone.
Figure 4:
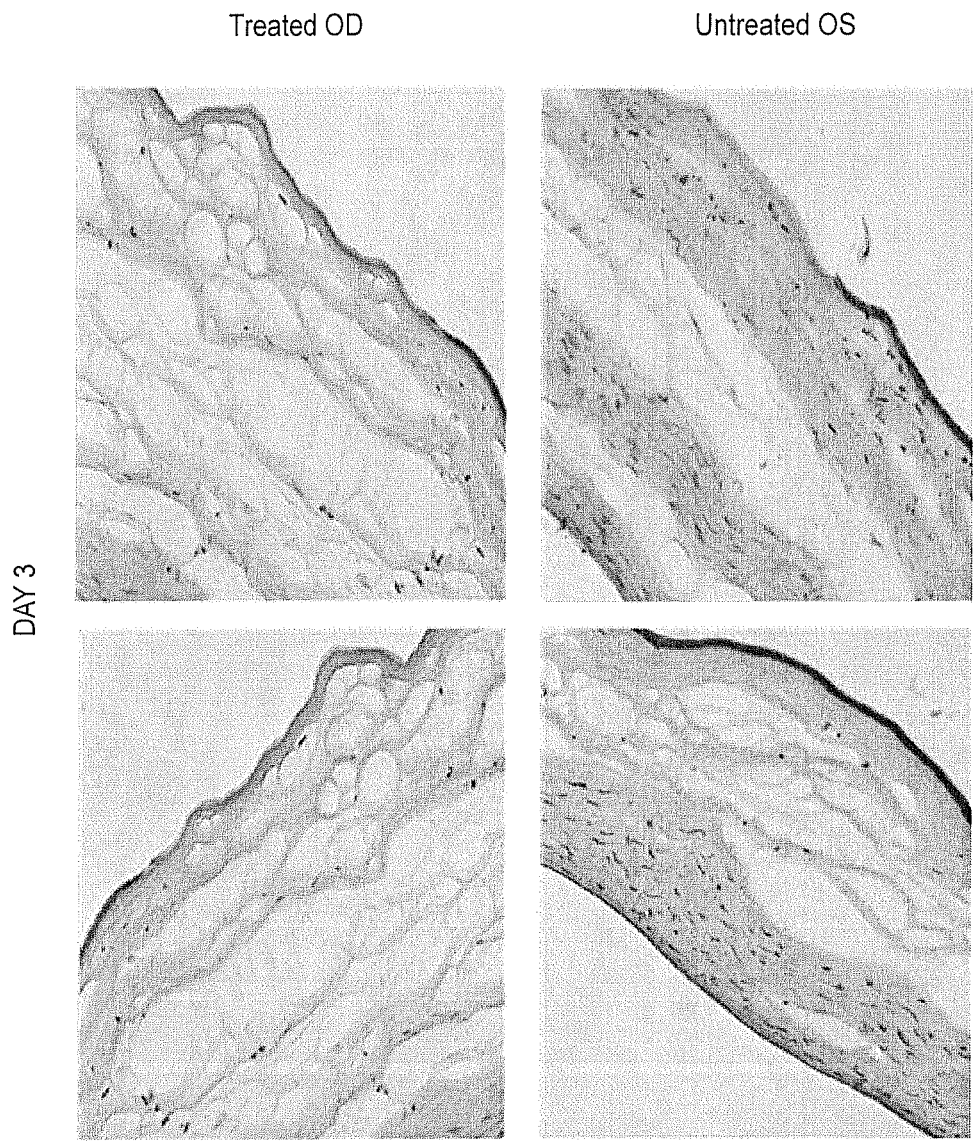
FIG. 4 is a montage of photomicrographs of histology sections showing treated and control corneal surfaces on the third day after hydrogel application, with arrowheads indicating the transition form epithelialized to de-epithelialized surfaces.

Examples 3 and 4, however, show an embodiment that was effective. The electrophilic functional group was changed to a faster-degrading succinimidyl succinate (8 arm 15K SS PEG), as shown in Table 3. Changes to the solids content did not create the same degree of changes in persistence time observed in Examples 1 and 2. FIG. 2 and Table 4 show the reduction in wound area over time for treated and control eyes, with the treated eyes having complete epithelial coverage on the same day as the untreated eyes. An unexpected result was observed: the epithelial cells were continuous with the hydrogel edges. FIG. 3 is a photomicrograph of histology slides taken at day 1 after hydrogel application. Panel (a) shows a de-epithelialized surface. Panel (b) shows the junction between the epithelialized surface and the de-epithelialized surface under the hydrogel. Panel (c) shows a portion of the hydrogel more towards its center, with no dehiscence or underlying epithelial cells. FIG. 4 shows a similar effect at day 3, although the hydrogel is not visible since it normally separates from the tissue during histological processing. The transition from epithelialization to non-coverage is visible for both treated and control eyes. Example 5 (see FIG. 7) is another example of a successful treatment, with the wound area being made by laser ablation.

Formation of hydrogels on an eye preferably provides for gelation to occur within about 0.1 to about 3 minutes; artisans will immediately appreciate that all the ranges and values within the explicitly stated ranges are contemplated, e.g., at least 10 seconds, or between 30 to 180 seconds. Gelation time is measured as described in the Examples.

Hydrogels

Now that this effect has been discovered and embodiments for achieving it described, artisans will be able to make alternative formulations. Accordingly, this embodiment of the invention is not to be limited to the particular examples. Moreover, further guidance is provided herein with respect to choices of materials and processes.

Furthermore, hydrogels as described herein may be used to treat conditions besides post-PRK. Other conditions include tissue damage caused by surgical or traumatic eye tissue removal. For instance, lasers and blades are used to re-shape eyes, e.g., laser-assisted in situ keratomileusis (LASIK) and Epi-LASIK.

Hydrogels are materials that do not dissolve in water and retain a significant fraction (more than 20%) of water within their structure. In fact, water contents in excess of 90% are often known. Hydrogels are often formed by crosslinking water soluble molecules to form networks of essentially infinite molecular weight. Hydrogels with high water contents are typically soft, pliable materials. A hydrogel that has been dried is referred to herein as a dehydrated hydrogel if it will return to a hydrogel state upon exposure to water (also referred to as a xerogel); this hydrogel that would expand in volume if it were exposed to an excess of water and not constrained. The term desiccated refers to a hydrogel essentially having no fluids, bearing in mind that some trace amounts of water may nonetheless be present.

Hydrogel Precursors

Hydrogels may be made from precursors. The precursors are not hydrogels but are covalently crosslinked with each other to form a hydrogel and are thereby part of the hydrogel. Crosslinks can be formed by covalent or ionic bonds, by hydrophobic association of precursor molecule segments, or by crystallization of precursor molecule segments. The precursors can be triggered to react to form a crosslinked hydrogel. The precursors can be polymerizable and include crosslinkers that are often, but not always, polymerizable precursors. Polymerizable precursors are thus precursors that have functional groups that react with each other to form polymers made of repeating units. Precursors may be polymers.

Some precursors thus react by chain-growth polymerization, also referred to as addition polymerization, and involve the linking together of monomers incorporating double or triple chemical bonds. These unsaturated monomers have extra internal bonds which are able to break and link up with other monomers to form the repeating chain. Monomers are polymerizable molecules with at least one group that reacts with other groups to form a polymer. A macromonomer (or macromer) is a polymer or oligomer that has at least one reactive group, often at the end, which enables it to act as a monomer; each macromonomer molecule is attached to the polymer by reaction the reactive group. Thus macromonomers with two or more monomers or other functional groups tend to form covalent crosslinks. Addition polymerization is involved in the manufacture of, e.g., polypropylene or polyvinyl chloride. One type of addition polymerization is living polymerization.

Some precursors thus react by condensation polymerization that occurs when monomers bond together through condensation reactions. Typically these reactions can be achieved through reacting molecules incorporating alcohol, amine or carboxylic acid (or other carboxyl derivative) functional groups. When an amine reacts with a carboxylic acid an amide or peptide bond is formed, with the release of water. Some condensation reactions follow a nucleophilic acyl substitution, e.g., as in U.S. Pat. No. 6,958,212, which is hereby incorporated by reference herein in its entirety to the extent it does not contradict what is explicitly disclosed herein.

Some precursors react by a chain growth mechanism. Chain growth polymers are defined as polymers formed by the reaction of monomers or macromonomers with a reactive center. A reactive center is a particular location within a chemical compound that is the initiator of a reaction in which the chemical is involved. In chain-growth polymer chemistry, this is also the point of propagation for a growing chain. The reactive center is commonly radical, anionic, or cationic in nature, but can also take other forms. Chain growth systems include free radical polymerization, which involves a process of initiation, propagation and termination. Initiation is the creation of free radicals necessary for propagation, as created from radical initiators, e.g., organic peroxide molecules. Termination occurs when a radical reacts in a way that prevents further propagation. The most common method of termination is by coupling where two radical species react with each other forming a single molecule.

Some precursors react by a step growth mechanism, and are polymers formed by the stepwise reaction between functional groups of monomers. Most step growth polymers are also classified as condensation polymers, but not all step growth polymers release condensates.

Monomers may be polymers or small molecules. A polymer is a high molecular weight molecule formed by combining many smaller molecules (monomers) in a regular pattern. Oligomers are polymers having less than about 20 monomeric repeat units. A small molecule generally refers to a molecule that is less than about 2000 Daltons.

The precursors must thus be small molecules, such as acrylic acid or vinyl caprolactam, larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, or U.S. Pat. Nos. 4,741,872 and 5,160,745 to DeLuca et al., each of which is hereby incorporated by reference herein in its entirety to the extent it does not contradict what is explicitly disclosed herein.

To form covalently crosslinked hydrogels, the precursors must be crosslinked together. In general, polymeric precursors will form polymers that will be joined to other polymeric precursors at two or more points, with each point being a linkage to the same or different polymers. Precursors with at least two reactive groups can serve as crosslinkers since each reactive group can participate in the formation of a different growing polymer chain. In the case of functional groups without a reactive center, among others, crosslinking requires three or more such functional groups on at least one of the precursor types. For instance, many electrophilic-nucleophilic reactions consume the electrophilic and nucleophilic functional groups so that a third functional group is needed for the precursor to form a crosslink. Such precursors thus may have three or more functional groups and may be crosslinked by precursors with two or more functional groups. A crosslinked molecule may be crosslinked via an ionic or covalent bond, a physical force, or other attraction. A covalent crosslink, however, will typically offer stability and predictability in reactant product architecture.

In some embodiments, each precursor is multifunctional, meaning that it comprises two or more electrophilic or nucleophilic functional groups, such that a nucleophilic functional group on one precursor may react with an electrophilic functional group on another precursor to form a covalent bond. At least one of the precursors comprises more than two functional groups, so that, as a result of electrophilic-nucleophilic reactions, the precursors combine to form crosslinked polymeric products.

The precursors may have biologically inert and hydrophilic portions, e.g., a core. In the case of a branched polymer, a core refers to a contiguous portion of a molecule joined to arms that extend from the core, with the arms having a functional group, which is often at the terminus of the branch. The hydrophilic precursor or precursor portion preferably has a solubility of at least 1 g/100 mL in an aqueous solution. A hydrophilic portion may be, for instance, a polyether, for example, polyalkylene oxides such as polyethylene glycol (PEG), polyethylene oxide (PEO), polyethylene oxide-co-polypropylene oxide (PPO), co-polyethylene oxide block or random copolymers, and polyvinyl alcohol (PVA), poly (vinyl pyrrolidinone) (PVP), poly (amino acids, dextran, or a protein. The precursors may have a polyalkylene glycol portion and may be polyethylene glycol based, with at least about 80% or 90% by weight of the polymer comprising polyethylene oxide repeats. The polyethers and more particularly poly (oxyalkylenes) or poly (ethylene glycol) or polyethylene glycol are generally hydrophilic.

A precursor may also be a macromolecule (or macromer), which is a molecule having a molecular weight in the range of a thousand to many millions. In some embodiments, however, at least one of the precursors is a small molecule of about 1000 Da or less. The macromolecule, when reacted in combination with a small molecule of about 1000 Da or less, is preferably at least five to fifty times greater in molecular weight than the small molecule and is preferably less than about 60,000 Da; artisans will immediately appreciate that all the ranges and values within the explicitly stated ranges are contemplated. A more preferred range is a macromolecule that is about seven to about thirty times greater in molecular weight than the crosslinker and a most preferred range is about ten to twenty times difference in weight. Further, a macromolecular molecular weight of 5,000 to 50,000 is useful, as is a molecular weight of 7,000 to 40,000 or a molecular weight of 10,000 to 20,000.

Certain macromeric precursors are the crosslinkable, biodegradable, water-soluble macromers described in U.S. Pat. No. 5,410,016 to Hubbell et al, which is hereby incorporated herein by reference in its entirety to the extent it does not contradict what is explicitly disclosed. These macromers are characterized by having at least two polymerizable groups, separated by at least one degradable region.

Synthetic precursors may be used. Synthetic refers to a molecule not found in nature or not normally found in a human. Some synthetic precursors are free of amino acids or free of amino acid sequences that occur in nature. Some synthetic precursors are polypeptides that are not found in nature or are not normally found in a human body, e.g., di-, tri-, or tetra-lysine. Some synthetic molecules have amino acid residues but only have one, two, or three that are contiguous, with the amino acids or clusters thereof being separated by non-natural polymers or groups. Polysaccharides or their derivatives are thus not synthetic.

Precursors may be made with a hydrophobic portion provided that the resultant hydrogel retains the requisite amount of water, e.g., at least about 20%. In some cases, the precursor is nonetheless soluble in water because it also has a hydrophilic portion. In other cases, the precursor makes dispersion in the water (a suspension) but is nonetheless reactable to from a crosslinked material. Some hydrophobic portions may include a plurality of alkyls, polypropylenes, alkyl chains, or other groups. Some precursors with hydrophobic portions are sold under the trade names PLURONIC F68, JEFFAMINE, or TECTRONIC. A hydrophobic portion is one that is sufficiently hydrophobic to cause the macromer or copolymer to aggregate to form micelles in an aqueous continuous phase or one that, when tested by itself, is sufficiently hydrophobic to precipitate from, or otherwise change phase while within, an aqueous solution of water at pH from about 7 to about 7.5 at temperatures from about 30 to about 50 degrees Centigrade.

Precursors may have, e.g., 2-100 arms, with each arm having a terminus, bearing in mind that some precursors may be dendrimers or other highly branched materials. An arm on a hydrogel precursor refers to a linear chain of chemical groups that connect a crosslinkable functional group to a polymer core. Some embodiments are precursors with between 3 and 300 arms; artisans will immediately appreciate that all the ranges and values within the explicitly stated ranges are contemplated, e.g., 4 to 16, 8 to 100, or at least 6 arms.

Thus hydrogels can be made, e.g., from a multi-armed precursor with a first set of functional groups and a low molecular-weight precursor having a second set of functional groups. For example, a six-armed or eight-armed precursor may have hydrophilic arms, e.g., polyethylene glycol, terminated with primary amines, with the molecular weight of the arms being about 1,000 to about 40,000; artisans will immediately appreciate that all ranges and values within the explicitly stated bounds are contemplated. Such precursors may be mixed with relatively smaller precursors, for example, molecules with a molecular weight of between about 100 and about 5000, or no more than about 800, 1000, 2000, or 5000 having at least about three functional groups, or between about 3 to about 16 functional groups; ordinary artisans will appreciate that all ranges and values between these explicitly articulated values are contemplated. Such small molecules may be polymers or non-polymers and natural or synthetic.

Precursors that are not dendrimers may be used. Dendritic molecules are highly branched radially symmetrical polymers in which the atoms are arranged in many arms and subarms radiating out from a central core. Dendrimers are characterized by their degree of structural perfection as based on the evaluation of both symmetry and polydispersity and require particular chemical processes to synthesize. Accordingly, an artisan can readily distinguish dendrimer precursors from non-dendrimer precursors. Dendrimers have a shape that is typically dependent on the solubility of its component polymers in a given environment, and can change substantially according to the solvent or solutes around it, e.g., changes in temperature, pH, or ion content.

Precursors may be dendrimers, e.g., as in Patent Application Pub. Nos. US20040086479, US20040131582, WO07005249, WO07001926, WO06031358, or the U.S. counterparts thereof; dendrimers may also be useful as multifunctional precursors, e.g., as in U.S. Pat. Pub. Nos. US20040131582, US20040086479 and PCT Applications No. WO06031388 and WO06031388; each of which US and PCT applications are hereby incorporated by reference herein in its entirety to the extent they do not contradict what is explicitly disclosed herein. Dendrimers are highly ordered possess high surface area to volume ratios, and exhibit numerous end groups for potential functionalization. Embodiments include multifunctional precursors that are not dendrimers.

Some embodiments include a precursor that consists essentially of an oligopeptide sequence of no more than five residues, e.g., amino acids comprising at least one amine, thiol, carboxyl, or hydroxyl side chain. A residue is an amino acid, either as occurring in nature or derivatized thereof. The backbone of such an oligopeptide may be natural or synthetic. In some embodiments, peptides of two or more amino acids are combined with a synthetic backbone to make a precursor; certain embodiments of such precursors have a molecular weight in the range of about 100 to about 10,000 or about 300 to about 500 Artisans will immediately appreciate that all ranges and values between these explicitly articulated bounds are contemplated.

Precursors may be prepared to be free of amino acid sequences cleavable by enzymes present at the site of introduction, including free of sequences susceptible to attach by metalloproteinases and/or collagenases. Further, precursors may be made to be free of all amino acids, or free of amino acid sequences of more than about 50, 30, 20, 10, 9, 8, 7, 6, 5, 4, 3, 2, or 1 amino acids. Precursors may be non-proteins, meaning that they are not a naturally occurring protein and can not be made by cleaving a naturally occurring protein and can not be made by adding synthetic materials to a protein. Precursors may be non-collagen, non-fibrin, non-fibrinogen), and non-albumin, meaning that they are not one of these proteins and are not chemical derivatives of one of these proteins. The use of non-protein precursors and limited use of amino acid sequences can be helpful for avoiding immune reactions, avoiding unwanted cell recognition, and avoiding the hazards associated with using proteins derived from natural sources. Precursors can also be non-saccharides (free of saccharides) or essentially non-saccharides (free of more than about 5% saccharides by w/w of the precursor molecular weight. Thus a precursor may, for example, exclude hyaluronic acid, heparin, or gellan. Precursors can also be both non-proteins and non-saccharides.

Peptides may be used as precursors. In general, peptides with less than about 10 residues are preferred, although larger sequences (e.g., proteins) may be used. Artisans will immediately appreciate that every range and value within these explicit bounds is included, e.g., 1-10, 2-9, 3-10, 1, 2, 3, 4, 5, 6, or 7. Some amino acids have nucleophilic groups (e.g., primary amines or thiols) or groups that can be derivatized as needed to incorporate nucleophilic groups or electrophilic groups (e.g., carboxyls or hydroxyls). Polyamino acid polymers generated synthetically are normally considered to be synthetic if they are not found in nature and are engineered not to be identical to naturally occurring biomolecules.

Some hydrogels are made with a polyethylene glycol-containing precursor. Polyethylene glycol (PEG, also referred to as polyethylene oxide when occurring in a high molecular weight) refers to a polymer with a repeat group $(CH_2CH_2O)_n$, with n being at least 3. A polymeric precursor having a polyethylene glycol thus has at least three of these repeat groups connected to each other in a linear series. The polyethylene glycol content of a polymer or arm is calculated by adding up all of the polyethylene glycol groups on the polymer or arm, even if they are interrupted by other groups. Thus, an arm having at least 1000 MW polyethylene glycol has enough $CH_2CH_2O$ groups to total at least 1000 MW. As is customary terminology in these arts, a polyethylene glycol polymer does not necessarily refer to a molecule that terminates in a hydroxyl group.

Functional Groups

The precursors have functional groups that react with each other to form the material, either outside a patient, or in situ. The functional groups generally have polymerizable groups for polymerization or react with each other in electrophile-nucleophile reactions or are configured to participate in other polymerization reactions. Various aspects of polymerization reactions are discussed in the precursors section herein.

Thus in some embodiments, precursors have a polymerizable group that is activated by photoinitiation or redox systems as used in the polymerization arts, e.g., or electrophilic functional groups that are carbodiimidazole, sulfonyl chloride, chlorocarbonates, n-hydroxysuccinimidyl ester, succinimidyl ester or sulfasuccinimidyl esters, or as in U.S. Pat. Nos. 5,410,016, or 6,149,931, each of which are hereby incorporated by reference herein in its entirety to the extent they do not contradict what is explicitly disclosed herein. The nucleophilic functional groups may be, for example, amine, hydroxyl, carboxyl, and thiol. Another class of electrophiles are acyls, e.g., as in U.S. Pat. No. 6,958,212, which describes, among other things, Michael addition schemes for reacting polymers.

Certain functional groups, such as alcohols or carboxylic acids, do not normally react with other functional groups, such as amines, under physiological conditions (e.g., pH 7.2-11.0, 37° C.). However, such functional groups can be made more reactive by using an activating group such as N-hydroxysuccinimide. Certain activating groups include carbonyldiimidazole, sulfonyl chloride, aryl halides, sulfosuccinimidyl esters, N-hydroxysuccinimidyl ester, succinimidyl ester, epoxide, aldehyde, maleimides, imidoesters and the like. The N-hydroxysuccinimide esters or N-hydroxysulfosuccinimide (NHS) groups are useful groups for crosslinking of proteins or amine-containing polymers, e.g., amino terminated polyethylene glycol. An advantage of an NHS-amine reaction is that the reaction kinetics are favorable, but the gelation rate may be adjusted through pH or concentration. The NHS-amine crosslinking reaction leads to formation of N-hydroxysuccinimide as a side product. Sulfonated or ethoxylated forms of N-hydroxysuccinimide have a relatively increased solubility in water and hence their rapid clearance from the body. An NHS-amine crosslinking reaction may be carried out in aqueous solutions and in the presence of buffers, e.g., phosphate buffer (pH 5.0-7.5), triethanolamine buffer (pH 7.5-9.0), or borate buffer (pH 9.0-12), or sodium bicarbonate buffer (pH 9.0-10.0). Aqueous solutions of NHS based crosslinkers and functional polymers preferably are made just before the crosslinking reaction due to reaction of NHS groups with water. The reaction rate of these groups may be delayed by keeping these solutions at lower pH (pH 4-7).

In some embodiments, each precursor comprises only nucleophilic or only electrophilic functional groups, so long as both nucleophilic and electrophilic precursors are used in the crosslinking reaction. Thus, for example, if a crosslinker has nucleophilic functional groups such as amines, the functional polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly(allyl amine), or amine-terminated di or multifunctional poly(ethylene glycol) can be used.

One embodiment has reactive precursor species with 3 to 16 nucleophilic functional groups each and reactive precursor species with 2 to 12 electrophilic functional groups each; artisans will immediately appreciate that all the ranges and values within the explicitly stated ranges are contemplated.

The functional groups may be, e.g., electrophiles reactable with nucleophiles, groups reactable with specific nucleophiles, e.g., primary amines, groups that form amide bonds with materials in the biological fluids, groups that form amide bonds with carboxyls, activated-acid functional groups, or a combination of the same. The functional groups may be, e.g., a strong electrophilic functional group, meaning an electrophilic functional group that effectively forms a covalent bond with a primary amine in aqueous solution at pH 9.0 at room temperature and pressure and/or an electrophilic group that reacts by a of Michael-type reaction. The strong electrophile may be of a type that does not participate in a Michaels-type reaction or of a type that participates in a Michaels-type reaction.

A Michael-type reaction refers to the 1,4 addition reaction of a nucleophile on a conjugate unsaturated system. The addition mechanism could be purely polar, or proceed through a radical-like intermediate state(s); Lewis acids or appropriately designed hydrogen bonding species can act as catalysts. The term conjugation can refer both to alternation of carbon-carbon, carbon-heteroatom or heteroatom-heteroatom multiple bonds with single bonds, or to the linking of a functional group to a macromolecule, such as synthetic polymer or a protein. Michael-type reactions are discussed in detail in U.S. Pat. No. 6,958,212, which is hereby incorporated by reference herein in its entirety for all purposes to the extent it does not contradict what is explicitly disclosed herein.

Examples of strong electrophiles that do not participate in a Michaels-type reaction are: succinimides, succinimidyl esters, or NHS-esters. Examples of Michael-type electrophiles are acrylates, methacrylates, methylmethacrylates, and other unsaturated polymerizable groups.

Hydrogels and Hydrogel Formation

In general, the precursors may be combined to make a covalently-crosslinked hydrogel. The hydrogel may comprise a therapeutic agent, or agents, released over a suitable period of time. Hydrogels may be made beforehand or in situ.

When made in situ, the crosslinking reactions generally occur in aqueous solution under physiological conditions. The crosslinking reactions preferably do not release heat of polymerization or require exogenous energy sources for initiation or to trigger polymerization. Photochemical initiation, for instance, is generally to be avoided in the eye so as to avoid damage to the eye.

The hydrogel may be generally low-swelling, as measurable by the hydrogel having a weight increasing no more than about 50% upon exposure to a physiological solution in the absence of physical restraints for twenty-four hours relative to a weight of the hydrogel at the time of formation. Swelling may be measured or expressed by weight or volume. Some embodiments swell by weight or by volume no more than about 50%, no more than about 20%, or no more than about 0%; artisans will immediately appreciate that all the ranges and values within the explicitly stated ranges are contemplated, e.g., shrinkage from 10% to 20% (negative swelling), swelling from −10% to no more than 50%. One aspect of swelling is that large changes will increase the difficulty of achieving a desired hydrogel size. For instance, filling a depression in a tissue with a swelling hydrogel will cause the hydrogel to have a height that is not apparent to the user at the time of application and/or gelation. Similarly, swelling (and shrinkage) can create forces that tend to pull the hydrogel away from surrounding tissues so that adherence is affected.

One approach for low-swelling is increase the number of crosslinks or solids content. Increasing in these factors, however, will typically effect the mechanical properties of the gel, with more crosslinks making the gel more brittle but stronger and a higher solids content making the gel stronger. These factors can also increase degradation time and may affect interactions with cells.

Unless otherwise indicated, swelling of a hydrogel relates to its change in volume (or weight) between the time of its formation when crosslinking is effectively complete and the time after being placed in in vitro aqueous solution in an unconstrained state for twenty-four hours, at which point it may be reasonably assumed to have achieved its equilibrium swelling state. For most embodiments, crosslinking is effectively complete within no more than about three minutes such that the initial weight can generally be noted at about 15 minutes after formation as Weight at initial formation. Accordingly, this formula is used: % swelling=[(Weight at 24 hours−Weight at initial formation)/Weight at initial formation]*100. The weight of the hydrogel includes the weight of the solution in the hydrogel.

Reaction kinetics are generally controlled in light of the particular functional groups, their concentrations, and the local pH unless an external initiator or chain transfer agent is required, in which case triggering the initiator or manipulating the transfer agent can be a controlling step. In some embodiments, the molecular weights of the precursors are used to affect reaction times. Precursors with lower molecular weights tend to speed the reaction due to their higher concentration of reactive groups, so that some embodiments have at least one precursor with a molecular weight of less than about 1000 or about 2000 Daltons; artisans will immediately appreciate that all the ranges and values within the explicitly stated ranges are contemplated, e.g., from 100 to about 900 Daltons or from 500 to about 1800 Daltons.

The crosslinking density of the resultant biocompatible crosslinked polymer is controlled by the overall molecular weight of the crosslinker and functional polymer and the number of functional groups available per molecule. A lower molecular weight between crosslinks such as 500 will give much higher crosslinking density as compared to a higher molecular weight such as 10,000. The crosslinking density also may be controlled by the overall percent solids of the crosslinker and functional polymer solutions. Increasing the percent solids increases the probability that an electrophilic functional group will combine with a nucleophilic functional group prior to inactivation by hydrolysis. Yet another method to control crosslink density is by adjusting the stoichiometry of nucleophilic functional groups to electrophilic functional groups. A one to one ratio leads to the highest crosslink density. Precursors with longer distances between crosslinks are generally softer, more compliant, and more elastic. Thus an increased length of a water-soluble segment, such as a polyethylene glycol, tends to enhance elasticity to produce desirable physical properties. Thus certain embodiments are directed to precursors with water soluble segments having molecular weights in the range of 3,000 to 100,000; artisans will immediately appreciate that all the ranges and values within the explicitly stated ranges are contemplated e.g., 10,000 to 35,000.

The solids content of the hydrogel can affect its mechanical properties and biocompatibility and reflects a balance between competing requirements. A relatively low solids content is useful, e.g., between about 2.5% to about 20%, including all ranges and values there between, e.g., about 2.5% to about 10%, about 5% to about 15%, or less than about 15%.

An embodiment for making a hydrogel in situ in the presence of a therapeutic agent is to combine precursors in an aqueous solution that can be administered with an applicator to the punctum and/or canaliculus and thereafter form the hydrogel. The precursors may be mixed with an activating agent before, during, or after administration. The hydrogel may be placed with a therapeutic agent dispersed therein, e.g., as a solution, suspension, particles, micelles, or encapsulated. Crosslinking, in one embodiment, entraps the agent. In another embodiment, the crosslinking causes the agent to precipitate or move from solution to suspension.

Thus one embodiment relates to combining a first hydrogel precursor with a first type of functional groups with a second hydrogel precursor having a second type of functional groups in an aqueous solvent in the presence of a therapeutic agent in the solvent. In one embodiment, the precursors are dissolved separately and combined in the presence of an activating agent that provides for effective crosslinking. Alternatively, the mere mixing of the precursors triggers crosslinking. Accordingly, one embodiment is providing branched polymer having a plurality of succinimidyl termini dissolved in a low pH (4.0) diluent solution) containing a low molecular weight precursor comprising nucleophiles. This solution is activated by combination with a higher pH solution (8.8), initiating the crosslinking mechanism. The agent is preloaded as a suspension in the diluent solution. The solution is applied to a canaliculus, or drawn into a small (e.g., 1 cc) syringe with a suitable cannula (e.g., 27 G) and injected into the canaliculus. The gel forms in situ.

Therapeutic Agents

A hydrogel network may be formed with a therapeutic agent optionally being present at the time of hydrogel network formation. The term therapeutic agent includes diagnostic agents, imaging agents, and drugs. The term drug refers to an agent intended to provoke a biological response so as to treat a patient. The hydrogels may be biodegradable or non-biodegradable.

The therapeutic agent may be dispersed (meaning spread substantially throughout a structure, either as a solution, suspension, or a colloid) within the hydrogel. The agent may be dispersed in the same phase as the fluid hydrating the hydrogel or it may be contained in a phase discontinuous from the fluid in the hydrogel. A phase discontinuous from the hydrogel may be a micelle, droplet, or a particle. Accordingly, a drug entrapped within microspheres dispersed within a hydrogel is a drug dispersed within the hydrogel. By way of contrast, a drug localized to a reservoir is not dispersed. A micelle, droplet, or a particle may include, for instance, a mixture of the drug with another material, e.g., a polymer. One embodiment of a particle is a capsule with the drug inside the capsule. Another embodiment of a particle is a solid formed by a polymer that associates with the drug. A particle may release a drug as it degrades, by diffusion, or a combination thereof. These features may be combined to provide a desired agent-release profile. A hydrogel with an agent dispersed through the hydrogel refers to a continuous hydrogel matrix with a substantially even distribution of agent throughout the structure.

An embodiment for making a hydrogel in situ in the presence of a therapeutic agent is to combine precursors in an aqueous solution that can be administered with an applicator to the eye and thereafter form the hydrogel. The precursors may be mixed with an activating agent before, during, or after administration. The hydrogel may be placed with a therapeutic agent dispersed therein, e.g., as a solution, suspension, particles, micelles, or encapsulated. Crosslinking, in one embodiment, entraps the agent. In another embodiment, the crosslinking causes the agent to precipitate or move from solution to suspension.

Thus one embodiment relates to combining a first hydrogel precursor with a first type of functional groups with a second hydrogel precursor having a second type of functional groups in an aqueous solvent in the presence of a therapeutic agent in the solvent. In one embodiment, the precursors are dissolved separately and combined in the presence of an activating agent that provides for effective crosslinking. Alternatively, the mere mixing of the precursors triggers crosslinking. Accordingly, one embodiment is providing branched polymer having a plurality of succinimidyl termini dissolved in a low pH (4.0) diluent solution) containing a low molecular weight precursor comprising nucleophiles. This solution is activated by combination with a higher pH solution (8.8), initiating the crosslinking mechanism. The agent is preloaded as a suspension in the diluent solution. The solution is applied to a eye, or drawn into a small (e.g., 1 cc) syringe with a suitable cannula (e.g., 27 G) and injected onto the eye. The gel forms in situ. Further options for application are detailed herein.

The hydrogels may include a therapeutic agent. Table 1 sets forth some embodiments of conditions and treatments. Methods include selecting a patient diagnosed with the indication, choosing a drug category or a specific drug, and delivering the drug with a hydrogel as set forth herein.

TABLE 1

Conditions and Corresponding Treatment.

| Item | Condition | Drug Class For Treatment | Examples |
|---|---|---|---|
| 1 | Dry Eye | Immunosuppressant | Cyclosporine A |
| 2 | Keratoconjunctivitis sicca | Immunosuppressant | Cyclosporine A |
|  |  | Anti-inflammatory | Prednisolone acetate |
| 3 | Blepharitis | Anti-inflammatory | Dexamethasone |
|  |  | Antibiotic | Tobramycin |
| 4 | Keratitis | Antibiotic | Moxifloxacin Gatifloxacin |
| 4 | Scleritis | Anti-inflammatory (NSAID) | Ibuprofen |
|  |  | Anti-inflammatory | Prednisolone acetate |
|  |  | Antibiotic | Moxifloxacin Gatifloxacin |
| 5 | Iritis | Anti-inflammatory | Prednisolone acetate |
| 6 | Uveitis | Anti-inflammatory | Prednisolone acetate |
| 7 | Conjunctivitis | Antibiotic | Moxifloxacin Gatifloxacin |
| 8 | Glaucoma | Prostaglandins | Latanoprost Travaprost |
|  |  | Beta Blockers | Timolol |
| 9 | Corneal Ulcer | Antibiotic | Moxifloxacin Gatifloxacin |
| 10 | Corneal Abrasion | Antibiotic | Moxifloxacin Gatifloxacin |
|  |  | Anticholinergic/ Cycloplegic | Atropine Tropicamide |

The hydrogel may be used to deliver classes of drugs including steroids, Non-steroidal anti-inflammatory drugs (NSAIDS), intraocular pressure lowering drugs, antibiotics, or others. The hydrogel may be used to deliver drugs and therapeutic agents, e.g., an anti-inflammatory (e.g., Diclofenac), a pain reliever (e.g., Bupivacaine), a Calcium channel blocker (e.g., Nifedipine), an Antibiotic (e.g., Ciprofloxacin), a Cell cycle inhibitor (e.g., Simvastatin), a protein (e.g., Insulin). The rate of release from the hydrogel will depend on the properties of the drug and the hydrogel, with factors including drug sizes, relative hydrophobicities, hydrogel density, hydrogel solids content, and the presence of other drug delivery motifs, e.g., microparticles.

The hydrogel may be used to deliver classes of drugs including steroids, NSAIDS), intraocular pressure lowering drugs, antibiotics, pain relievers, inhibitors or vascular endothelial growth factor (VEGF), chemotherapeutics, anti viral drugs etc. The drugs themselves may be small molecules, proteins, RNA fragments, proteins, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides, or other configurations. The drugs that have low water solubility may be incorporated, e.g., as particulates or as a suspension. Higher water solubility drugs may be loaded within microparticles or liposomes. Microparticles can be formed from, e.g., PLGA or fatty acids. Examples of NSAIDS are Ibuprofen, Meclofenamate sodium, mefanamic acid, salsalate, sulindac, tolmetin sodium, ketoprofen, diflunisal, piroxicam, naproxen, etodolac, flurbiprofen, fenoprofen calcium, Indomethacin, celoxib, ketrolac, and nepafenac.

A variety of drugs or other therapeutic agents may be delivered using these systems. A list of agents or families of drugs and examples of indications for the agents are provided. The agents may also be used as part of a method of treating the indicated condition or making a composition for treating the indicated condition. For example, AZOPT (a brinzolamide opthalmic suspension) may be used for treatment of elevated intraocular pressure in patients with ocular hypertension or open-angle glaucoma. BETADINE in a Povidone-iodine ophthalmic solution may be used for prepping of the periocular region and irrigation of the ocular surface. BETOPTIC (betaxolol HCl) may be used to lower intraocular pressure, or for chronic open-angle glaucoma and/or ocular hypertension. CILOXAN (Ciprofloxacin HCl opthalmic solution) may be used to treat infections caused by susceptible strains of microorganisms. NATACYN (Natamycin opthalmic suspension) may be used for treatment of fungal blepharitis, conjunctivitis, and keratitis. NEVANAC (Nepanfenac opthalmic suspension) may be used for treatment of pain and inflammation associated with cataract surgery. TRAVATAN (Travoprost ophthalmic solution) may be used for reduction of elevated intraocular pressure—open-angle glaucoma or ocular hypertension. FML FORTE (Fluorometholone ophthalmic suspension) may be used for treatment of corticosteroid-responsive inflammation of the palperbral and bulbar conjunctiva, cornea and anterior segment of the globe. LUMIGAN (Bimatoprost ophthalmic solution) may be used for reduction of elevated intraocular pressure—open-angle glaucoma or ocular hypertension. PRED FORTE (Prednisolone acetate) may be used for treatment of steroid-responsive inflammation of the palpebral and bulbar conjunctiva, cornea and anterior segment of the globe. PROPINE (Dipivefrin hydrochloride) may be used for control of intraocular pressure in chronic open-angle glaucoma. RESTASIS (Cyclosporine ophthalmic emulsion) may be used to increases tear production in patients, e.g., those with ocular inflammation associated with keratoconjunctivitis sicca. ALREX (Loteprednol etabonate ophthalmic suspension) may be used for temporary relief of seasonal allergic conjunctivitis. LOTEMAX (Loteprednol etabonate ophthalmic suspension) may be used for treatment of steroid-responsive inflammation of the palpebral and bulbar conjunctiva, cornea and anterior segment of the globe. MACUGEN (Pegaptanib sodium injection) may be used for Treatment of neovascular (wet) age-related macular degeneration. OPTIVAR (Azelastine hydrochloride) may be used for treatment of itching of the eye associated with allergic conjunctivitis. XALATAN (Latanoprost ophthalmic solution) may be used to reduce elevated intraocular pressure in patients, e.g., with open-angle glaucoma or ocular hypertension. BETIMOL (Timolol opthalmic solution) may be used for treatment of elevated intraocular pressure in patients with ocular hypertension or open-angle glaucoma. Latanoprost is the pro-drug of the free acid form, which is a prostanoid selective FP receptor agonist. Latanoprost reduces intraocular pressure in glaucoma patients with few side effects. Latanoprost has a relatively low solubility in aqueous solutions, but is readily soluble in organic solvents typically employed for fabrication of microspheres using solvent evaporation.

One embodiment comprises extended release of a medication for allergic conjunctivitis. For instance, ketotifen, an antihistamine and mast cell stabilizer, may be released to the eye as described herein in effective amounts to treat allergic conjunctivitis. Seasonal Allergic Conjunctivitis (SAC) and Perennial Allergic Conjunctivitis (PAC) are allergic conjunctival disorders. Symptoms include itching and pink to reddish eyes. These two eye conditions are mediated by mast cells. Non specific measures to ameliorate symptoms conventionally include: cold compresses, eyewashes with tear substitutes, and avoidance of allergens. Treatment conventionally consists of antihistamine mast cell stabilizers, dual mechanism anti-allergen agents, or topical antihistamines. Corticosteroids might be effective but, because of side effects, are reserved for more severe forms of allergic conjunctivitis such as vernal keratoconjunctivitis (VKC) and atopic keratoconjunctivitis (AKC).

Moxifloxacin is the active ingredient in VIGAMOX, which is a fluoroquinolone approved for use to treat or prevent ophthalmic bacterial infections. Dosage is typically one-drop of a 0.5% solution that is administered 3 times a day for a period of one-week or more.

VKC and AKC are chronic allergic diseases where eosinophils, conjunctival fibroblasts, epithelial cells, mast cells, and/or TH2 lymphocytes aggravate the biochemistry and histology of the conjunctiva. VKC and AKC can be treated by medications used to combat allergic conjunctivitis.

Accordingly, embodiments include hydrogels that incorporate one or more of the agents. The agents may be incorporated using one or more processes herein, e.g., with or without microspheres. The hydrogels may be used to make medicaments for administration of an effective amount of the agent over a predetermined time to treat the conditions indicated.

Some therapeutic agents are visualization agents. A visualization agent may be used with a hydrogel; it reflects or emits light at a wavelength detectable to a human eye so that a user applying the hydrogel can observe the gel. Some useful visualization agents are FD&C BLUE #1, FD&C BLUE #2, and methylene blue. Such agents may be used with microsphere and/or hydrogel embodiments set forth herein.

These agents, when dispersed in a hydrogel, are preferably present at a concentration of more than 0.05 mg/ml and preferably in a concentration range of at least 0.1 to about 12 mg/ml, and more preferably in the range of 0.1 to 4.0 mg/ml, although greater concentrations may potentially be used, up to the limit of solubility of the visualization agent. These concentration ranges can give a color to the hydrogel without interfering with crosslinking times for electrophilic-nucleophilic reactive precursor embodiments (as measured by the time for the reactive precursor species to gel).

Visualization agents may be selected from among any of the various non-toxic colored substances suitable for use in medical implantable medical devices, such as FD&C BLUE dyes 3 and 6, eosin, methylene blue, indocyanine green or colored dyes normally found in synthetic surgical sutures. The visualization agent may be present with either reactive precursor species, e.g., a crosslinker or functional polymer solution. The preferred colored substance may or may not become chemically bound to the hydrogel. The visualization agent may generally be used in small quantities, preferably less than 1% weight/volume, more preferably less that 0.01% weight/volume and most preferably less than 0.001% weight/volume concentration.

Additional machine-aided imaging agents may be used, such as fluorescent compounds, x-ray contrast agents (e.g., iodinated compounds) for imaging under x-ray imaging equipment, ultrasonic contrast agents, or MRI contrast agents (e.g., Gadolinium containing compounds).

Compositions have been formulated to use visualization agents with advantages that were unexpected. One is that a user can see the gel on the applicator to ensure adequate material for covering the tissue is present, another is the user can see the gel when it is applied but, after application and spreading of the solution, the patient does not detect the coloration spread in a thin layer across the eye.

Phase Separation of Agents for Delivery

In some embodiments, the therapeutic agent or agents are present in a separate phase when precursor(s) are reacted to produce a crosslinked polymer hydrogel. This phase separation prevents participation of therapeutic agents in the chemical crosslinking reaction such as reaction between N-hydroxysuccinimide (NHS ester) and amine group. The separate phase also helps to modulate the release kinetics of active agent from the crosslinked material or gel, where 'separate phase' could be oil (oil-in water emulsion), biodegradable vehicle, and the like. Biodegradable vehicles in which the active agent may be present include: encapsulation vehicles, such as microparticles, microspheres, microbeads, micropellets, and the like, where the active agent is encapsulated in a bioerodable or bioresorbable polymer such as polymers and copolymers of: poly(anhydride), poly(hydroxy acid)s, poly(lactone)s, poly(trimethylene carbonate), poly(glycolic acid), poly(lactic acid), poly(glycolic acid)-co-poly(glycolic acid), poly(orthocarbonate), poly(caprolactone), caging and entrapping molecules, like cyclodextrin, molecular sieves and the like. Microspheres made from polymers and copolymers of poly(lactone)s and poly(hydroxy acid)s are useful biodegradable encapsulation vehicles.

Certain embodiments of the invention are accomplished by providing compositions and methods to control the release of relatively low molecular weight therapeutic species using hydrogels. A therapeutic agent first is dispersed or dissolved within one or more relatively hydrophobic rate modifying agents to form a mixture. The mixture may be formed into particles or microparticles, which are then entrapped within a bioabsorbable hydrogel matrix so as to release the water soluble therapeutic agents in a controlled fashion. Alternatively, the microparticles may be formed in situ during crosslinking of the hydrogel. Drugs can be encapsulated using a variety of techniques for the purpose of controlled release prior to incorporation into a hydrogel. These controlled release systems may be forms of suspensions, oil solutions, emulsions, liposomes, micelles, implants and microparticles. Polymeric controlled release systems are commonly used in the pharmaceutical industry to provide sustained release with well over a dozen marketed products based on biodegradable polymers. Synthetic forms of biodegradable polymers may include polyorthoesters, polyanhydrides, polyphosazenes, polyamino acids polyalkylcyanoacrylates, polyesters (such as polycaprolactone, polydioxanone, polytrimethylenecarbonate, etc.), and the more frequently employed polyesters (poly(lactide)(PLA) and poly(lactide-co-glycolide) (PLGA)).

With respect to microparticle fabrication techniques, hydrophilic drugs are typically incorporated in the inner aqueous phase (see multiple emulsion method) or as solids dispersed in the oil phase (see dispersion method), whereas lipophilic drugs are generally dissolved in the organic/oil phase (see cosolvent method). With respect to solvent casting, the drugs are incorporated similarly to the cosolvent method minus the continuous phase necessary for microparticle formation. With respect to melt extrusion or compression techniques, the drugs may be incorporated in their initial state in the absence of solvent. Variations of these incorporation techniques exist and may be adjusted, as multiple variables (e.g., drug loading, solubility, solvent selection and blends, polymer concentration, polymer type and blends, excipients, targeted release duration, drug stability) play a role in selecting the best choice to incorporate the drug into the polymer matrix.

In one method, hydrogel microspheres are formed from polymerizable macromers or monomers by dispersion of a polymerizable phase in a second immiscible phase, wherein the polymerizable phase contains at least one component required to initiate polymerization that leads to crosslinking and the immiscible bulk phase contains another component required to initiate crosslinking, along with a phase transfer agent. Pre-formed microparticles containing the water soluble therapeutic agent may be dispersed in the polymerizable phase, or formed in situ, to form an emulsion. Polymerization and crosslinking of the emulsion and the immiscible phase is initiated in a controlled fashion after dispersal of the polymerizable phase into appropriately sized microspheres, thus entrapping the microparticles in the hydrogel microspheres. Visualization agents may be included, for instance, in the microspheres, microparticles, and/or microdroplets.

Embodiments of the invention include compositions and methods for forming composite hydrogel-based matrices and microspheres having entrapped therapeutic compounds. In one embodiment, a bioactive agent is entrapped in microparticles having a hydrophobic nature (also termed hydrophobic microdomains), to retard leakage of the entrapped agent. In some cases, the composite materials that have two phase dispersions, where both phases are absorbable, but are not miscible. For example, the continuous phase may be a hydrophilic network (such as a hydrogel, which may or may not be crosslinked) while the dispersed phase may be hydrophobic (such as an oil, fat, fatty acid, wax, fluorocarbon, or other synthetic or natural water immiscible phase, generically referred to herein as an "oil" or "hydrophobic" phase).

The oil phase entraps the drug and provides a barrier to release by slow partitioning of the drug into the hydrogel. The hydrogel phase in turn protects the oil from digestion by enzymes, such as lipases, and from dissolution by naturally occurring lipids and surfactants. The latter are expected to have only limited penetration into the hydrogel, for example, due to hydrophobicity, molecular weight, conformation, diffusion resistance, etc. In the case of a hydrophobic drug which has limited solubility in the hydrogel matrix, the particulate form of the drug may also serve as the release rate modifying agent.

Hydrophobic microdomains, by themselves, may be degraded or quickly cleared when administered in vivo, making it difficult to achieve prolonged release directly using microdroplets or microparticles containing the entrapped agent in vivo. In accordance with the present invention, however, the hydrophobic microdomains are sequestered in a gel matrix. The gel matrix protects the hydrophobic microdomains from rapid clearance, but does not impair the ability of the microdroplets or microparticles to release their contents slowly. Visualization agents may be included, for instance, in the gel matrix or the microdomains.

In one embodiment, a microemulsion of a hydrophobic phase and an aqueous solution of a water soluble molecular compound, such as a protein, peptide or other water soluble chemical is prepared. The emulsion is of the "water-in-oil" type (with oil as the continuous phase) as opposed to an "oil-in-water" system (where water is the continuous phase). Other aspects of drug delivery are found in U.S. Pat. Nos. 6,632,457; 6,379,373; and 6,514,534, each of which are hereby incorporated by reference herein in its entirety. Moreover, drug delivery schemes as described in U.S. Ser. No. 12/012,808 filed Feb. 6, 2008 and its priority document 60/899,898 filed Feb. 6, 2007, which are each hereby incorporated by reference herein in its entirety, and accordingly may also be used with the hydrogels and particles herein.

Controlled rates of therapeutic agent delivery also may be obtained with the system disclosed herein by degradable, covalent attachment of the therapeutic agents to the crosslinked hydrogel network. The nature of the covalent attachment can be controlled to enable control of the release rate from hours to weeks or longer. By using a composite made from multiple linkages with a range of hydrolysis times, a controlled release profile may be extended for longer durations.

Agents can be encapsulated using a variety of techniques for the purpose of controlled release for incorporation into the hydrogels, e.g., by mixing into the solution of precursors applied to an eye. For instance, the agents may be placed in a depot or in a diluent or a separate solution mixed with the precursors. These controlled release systems may be forms of suspensions, oil solutions, emulsions, liposomes, micelles, implants and microparticles. Polymeric controlled release systems are commonly used in the pharmaceutical industry to provide sustained release with well over a dozen marketed products based on biodegradable polymers. Synthetic forms of biodegradable polymers may include polyorthoesters, polyanhydrides, polyphosazenes, polyamino acids polyalkylcyanoacrylates, polyesters (such as polycaprolactone, polydioxanone, polytrimethylenecarbonate, etc.), and the more frequently employed polyesters (poly(lactide)(PLA) and poly(lactide-co-glycolide) (PLGA)).

Polyesters such as poly(lactide) (PLA) and its glycolic acid copolymer poly(lactide-co-glycolide) (PLGA) may be used as a drug carrier due to their biocompatibility, biodegradability and mechanical strength. They degrade by hydrolysis of the ester backbone and their degradation products (i.e. lactic and glycolic acids) are metabolic compounds. Degradation by hydrolysis refers to the spontaneous breaking of covalent bonds in water without a role for enzymes; hydrolytically degradable materials thus will degrade over time in a solution of water that is free of enzymes. Polyesters such as poly (lactide) (PLA) and its glycolic acid copolymer poly(lactide-co-glycolide) (PLGA) are most commonly used as a drug carrier due to their excellent biocompatibility, biodegradability and mechanical strength. They degrade by hydrolysis of the ester backbone and their degradation products (i.e. lactic and glycolic acids) are metabolic compounds. Incorporation of drug into polyesters can be performed using a variety of techniques, such as: melt extrusion, compression, solvent casting, injection molding, in situ polymerization and micro and/or nanoparticles. Microparticles can be formed by granulation of the aforementioned extruded, compressed or cast polymer systems, or they can be formed using techniques such as: spray drying, spray-freeze drying, phase separation (coacervation) and solvent evaporation. Solvent evaporation may employ techniques, to encapsulate the drug dependent upon the lipophilicity and/or hydrophilicity of the drug.

Incorporation of agents into polyesters can be performed using a variety of techniques, such as: melt extrusion, compression, solvent casting, injection molding, in-situ polymerization and micro and/or nanoparticles. Microparticles can be formed by granulation of the aforementioned extruded, compressed or cast polymer systems, or they can be formed using techniques such as: spray drying, spray-freeze drying, phase separation (coacervation) and solvent evaporation. Solvent evaporation may employ different techniques to encapsulate the drug dependent upon the lipophilicity and/or hydrophilicity of the agent.

With respect to microparticle fabrication techniques, hydrophilic agents are typically incorporated in the inner aqueous phase or as solids dispersed in the oil phase, whereas lipophilic agents are generally dissolved in the organic/oil phase (see cosolvent. With respect to solvent casting, the agents are incorporated similarly to the cosolvent method minus the continuous phase necessary for microparticle formation. With respect to melt extrusion or compression techniques, the agents are generally incorporated in their initial state in the absence of solvent. Variations of these incorporation techniques exist and should be adjusted on a case-by-case basis, as multiple variables (e.g., drug loading, solubility, solvent selection and blends, polymer concentration, polymer type and blends, excipients, targeted release duration, drug stability, etc.) play a role in selecting the best choice to incorporate the drug into the polymer matrix. U.S. Ser. No. 12/704, 692 filed Feb. 12, 2010 is hereby incorporated herein by reference for all purposes; in case of conflict the instant specification controls.

Biodegradation

The hydrogel is, in general, water-degradable, as measurable by the hydrogel being dissolvable in vitro in an excess of water by degradation of water-degradable groups. This test is predictive of hydrolytically-driven dissolution in vivo, a process that is in contrast to cell or protease-driven degradation. Significantly, however, polyanhydrides or other conventionally-used degradable materials that degrade to acidic components tend to cause inflammation in the eye. The hydrogels, however, may exclude such materials, and may be free of polyanhydrides, anhydride bonds, or precursors that degrade into acid or diacids. Instead, for example, SG (succinimidyl glutarate), SS (succinimidyl succinate), SC (succinimidyl carbonate), SAP (succinimidyl adipate), carboxymethyl hydroxybutyric acid (CM-HBA) may be used and have esteric linkages that are hydrolytically labile. More hydrophobic linkages such as suberate linkages may also be used, with these linkages being less degradable than succinate, glutarate or adipate linkages.

The crosslinked hydrogel degradation will generally proceed by the water-driven hydrolysis of the biodegradable segment when water-degradable materials are used. Polymers that include ester linkages may also be included to provide a desired degradation rate, with groups being added or subtracted near the esters to increase or decrease the rate of degradation. Thus it is possible to construct a hydrogel with a desired degradation profile, from a few days to many months, using a degradable segment.

Application

Embodiments include hydrogels as described herein for treatment of a tissue. The hydrogels may be homogeneous, i.e., may be made and used as a single material, meaning that they are made with one matrix material that is the same throughout, e.g., with no added coverings, sleeves, sheathes, overcoats, reservoir portions, or other added materials. Some embodiments are made with a uniform macroscopic structure such that they have no openings into the hydrogel, i.e., the material lacks tunnels or macro-pore structures, bearing in mind that a hydrogel will have a certain native porosity. A homogenous hydrogel may include agents dispersed therein.

The covalently crosslinked hydrogels have advantages over non-crosslinked hydrogels that are not conventionally appreciated. One advantage is that coacervates (alginate) or ionic crosslinks tend to break and re-form as the gel is strained such that there is a permanent shape-change. Thus water can be squeezed out of such materials in an ocular setting. But the covalently crosslinked hydrogels absorb water and do not re-form their crosslinks in response to a strain. The covalent crosslinking also may be used to provide for a gel with structural strength that allows firm grasping and forceful removal by forceps or tools even when hydrated. Accordingly, methods include manual retrieval of a hydrogel after its application, including retrieval for patients experiencing a poor response or the recovery of non-degradable hydrogels or hydrogels designed to degrade at a point longer than the intended time of hydrogel use.

An embodiment of a system for applying a hydrogel as set forth herein is described. In this embodiment, a tray with a well is provided. In a two precursor system, one of the precursors is applied to a first portion of the well to form a first deposit and another of the precursors is applied to a separate portion of the well. Further precursors may be combined with one or more of the deposits or applied as an nth deposit. A volume of purified water or an aqueous solution with buffers or other materials is delivered to one or more of the deposits. The deposit(s) are allowed to dissolve in the volume and then mixed together with a mixing rod. The term mixing rod is broad and includes embodiments that are equivalent to the rod for mixing small volumes, e.g., spoons, spears, tubes. The precursors, when spontaneously reactive with each other, begin to crosslink to form the hydrogel. An applicator with a delivery surface is introduced into the mixture and picks up a desired volume. A user then transfers some, or the greater part of the volume, or substantially all of the volume, to an eye.

The term delivery surface sized to hold a volume of no more than about 100 µl of a liquid volume means that dipping the surface into a body of pure distilled water and withdrawing the surface recovers no more than about 100 µl of the water. The term delivery surface refers to a discrete surface in its entirety. In the context of a device, the delivery surface can be well understood by the artisan; for instance a sponge or brush on the end of a mixing rod, or the portion that holds the volume when used as intended when transferring from a liquid to an eye. The term transfer in the context of use with a delivery surface means that the volume that is held by the applicator has to be substantially transferred, or transferable, to an eye, which is a delicate tissue. For the sake of clarity these terms are to be tested in the context of holding and transferring pure distilled water. Accordingly, a cotton ball will not substantially transfer the volume of water because it tends to absorb the water. On the other hand a small brush can hold the volume of water and transfer the greater portion of the volume.

As is correspondingly set forth in U.S. Ser. No. 12/012,606 filed Feb. 2, 2008, which is hereby incorporated by reference herein for all purposes (in the case of conflict the instant specification controls), a delivery surface is configured to provide a controllable amount of solution in a predetermined volume range so that the user can conveniently pick up as much solution as is reasonably needed; not too much and not too little. For instance, the delivery surface can be sized and proportioned to provide a drop in a range or subrange from about 5 microliters to about 500 microliters; artisans will immediately appreciate that all the ranges and values within the explicitly stated ranges are contemplated, e.g., from about 5 microliters to about 100 microliters, from about 20 microliters to about 200 microliters, less than about 100 microliters, or less than about 50 microliters. Such a range can be controlled by providing a taper, surface area, and hydrophobicity of the tip in light of a density of the solution; for instance, a surface that is relatively hydrophobic can cause the solution to bead and form a drop as opposed to spreading more broadly on the surface to provide a larger drop size. The surface area of the delivery surface, and consequently the size of the surface, as well as its hydrophobicity control the size of the droplet volume that is naturally picked up. Some embodiments further control a size of droplet pickup by capillary forces created by including a feature on the applicator tip. Such feature may be, for example, a dimple, a crescent, a groove, a slit, a slot or other indentation.

In general, for delicate tissues, e.g., a cornea, the applicator delivery surface may be of a type that is atraumatic to the corneal or other delicate tissue surfaces, so as to not induce trauma, such as a corneal abrasion during normal application manipulation. A closed cell foam is suited for the material of the applicator tip. Also suitable is a hydrophobic closed cell foam, such as a polyethylene foam. Another embodiment is a (soft) brush that is sized to hold a suitable volume without retaining the greater part of it. The applicator delivery surface may be designed to not absorb a significant portion of liquid by itself, since this can create variability in the amount of material delivered to the application site. The amount needed to be delivered may be less than 10 microliters, which is smaller than one drop; for instance, opthalmic sealant applications typically require small volumes of materials. If the applicator delivery surface is made from a sponge or other material that absorb a significant amount of the liquid, then the application will have variability. Application of too much of a material, e.g., as in a hydrogel to the surface of the cornea, can create patient discomfort. Accordingly, delivery surfaces may be chosen that absorb less than about 30%, less than about 20%, less than about 10%, or essentially 0% of a solution's volume, including the case wherein the volume is less than: about 100, about 50, about 20, or about 10 microliters. As is apparent, embodiments of the applicator may have one or more of these features.

Dropper is a broad term that refers to a device that can deliver drops. Alternatives include bulbous droppers and pipettes or pipetting systems, e.g, as in U.S. Pat. Nos. 703, 101, 3,158,183, 4,117,728, or 5,154,702, each of which are hereby incorporated by reference herein to the extent they do not contradict what is explicitly disclosed. Another embodiment is an ampoule with a cap that covers an opening sized to deliver its contents in small volumes, e.g., dropwise In general, users can manually perform dropwise dispensing with good accuracy using a suitable dropper. Single-use droppers are generally convenient for purposes of sterility.

While a two-precursor system is described in detail, embodiments nonetheless include variations wherein one precursor or all precursors are provided in one deposit and other components are provided in another deposit or in an aqueous solution for mixing with the deposit. For instance, the precursors may be placed in one deposit with buffering agents as needed to provide for a slow reaction and then mixed with buffers that change the pH or other accelerants for the reaction that provide for an increase in reaction rate after introduction to the precursors. The various precursors and hydrogel-forming compositions set forth herein may, accordingly, be used.

Figure 5:
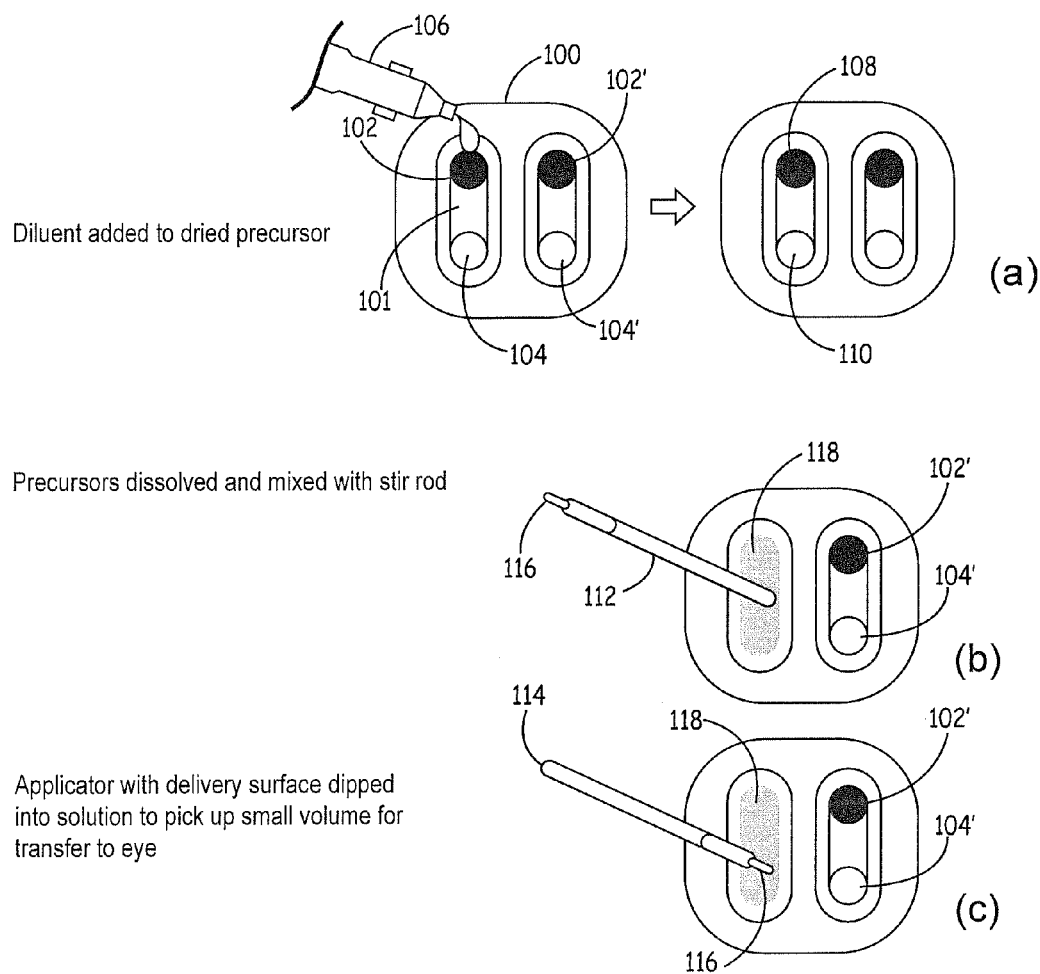
FIG. 5 depicts a system for application of hydrogels to an eye.

An embodiment of one such system is set forth in FIG. 5. Tray 100 has well 101 with first deposit 102 and second deposit 104. A second well and deposits 102', 104' are provided for redundancy. A dropper 106 is used to apply a drop of aqueous solution to deposits 102, 104 to make solutions 108, 110. Applicator 112 has mixing rod 114 on one end and delivery surface 116 (a brush) on the opposing end. A user optionally mixes one or more of the deposits with the mixing rod to make sure it is in solution and then mixes solutions 108, 110 with each other to form mixture 118. The user then picks up a volume of the mixture from well 101 with the delivery surface 116 and subsequently transfers at least a portion of the mixture to an intended site of delivery on a patient's tissue, e.g., the cornea or a de-epithelialized zone.

Trays may be made of mechanically suitable materials, e.g., engineering polymers, polycarbonate, polyethylene, polypropylene, TYVEK, or polyether ether ketone. There may be one or more wells. Precursors may be dried from aqueous or organic solutions or alcohols, freeze-dried or lyophilized. Kits may be made to house the components within a single sterile housing, e.g., covered tray, pouch, or packaging. The housing may be, for instance, a box, pouch, plastic container, or some combination thereof. In general, the housing is designed for, and made of materials for, sterilization by conventional medical methods, e.g., radiation or ethylene oxide.

Various embodiments of an ocular bandage, including coatings, layers, hydrogels, and pre-formed materials are described herein. As is evident, these embodiments of materials applied to an eye may be used as a complete bandage solution, and without further structures. Accordingly, such materials may be used in systems and methods that, after being applied, are free of lenses, molds, hard materials (glass, engineering plastics), additional refractive materials, and additional layers or coatings. Further, as is evident in context, embodiments are described that have no more than one layer of a material, with the hydrogel or other material providing the complete bandage. Accordingly, a layer or a hydrogel may be provided that has a surface applied to an eye and an opposing surface in contact with the eyelid when the eyelid is closed over the eye. As described below, some embodiments comprise two layers with the first layer contacting an eye and a second layer, with the second layer contacting the first layer and having an opposing surface that is in contact with an eyelid when the eyelid is closed.

Figure 6A:
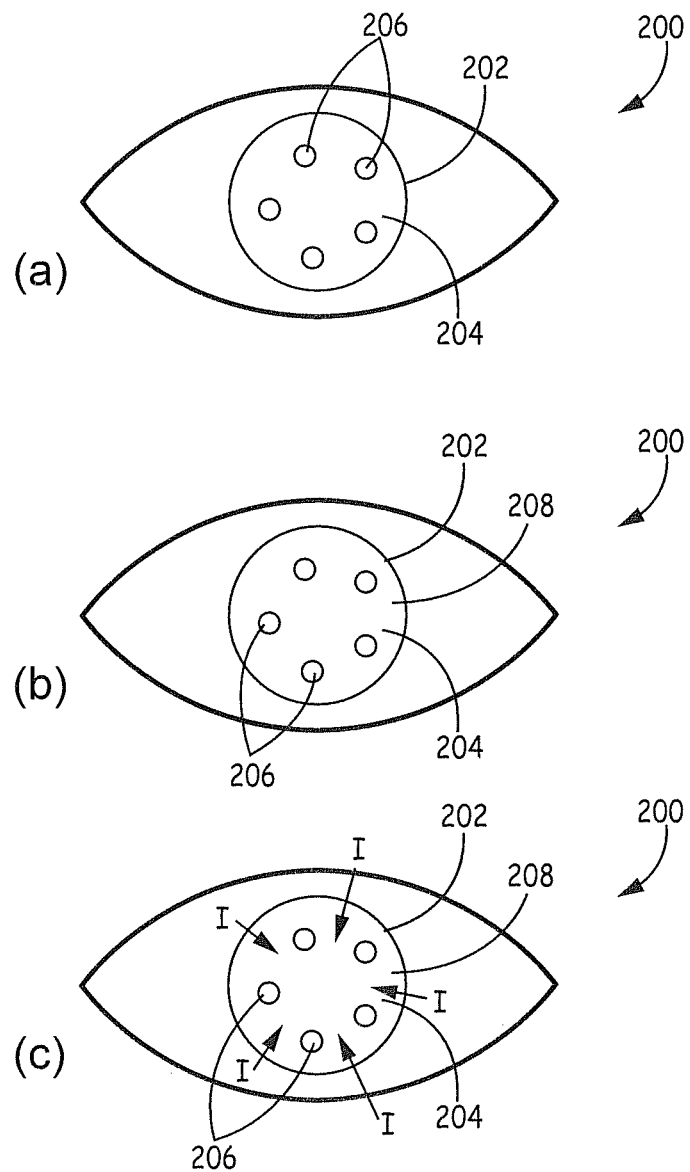
FIG. 6A depicts an application of materials to an eye with a masking approach.
Figure 6B:
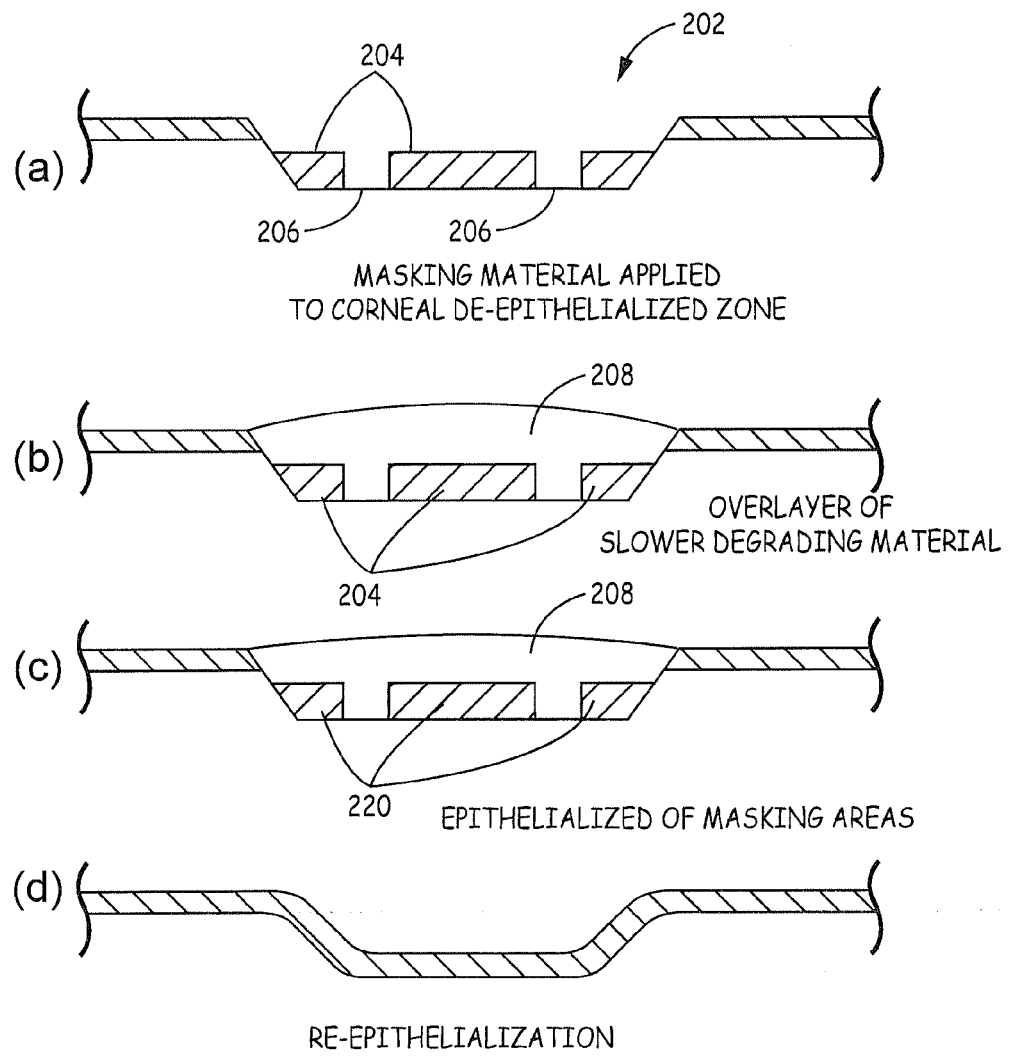
FIG. 6B depicts a healing process for the embodiment of FIG. 6A.

Another system and method for treating a defect is illustrated in FIG. 6. At FIG. 6A, eye 200 has wounded area 202 with a first fast-degrading layer 204 (also referred to as a masking layer) applied thereupon excepting a plurality of uncoated locations 206 (also referred to as tie points). At panel (b), a second layer 208 is applied thereupon, which covers the first layer and also the locations 206. The second layer degrades more slowly than the first layer, so that degradation of the first layer provides ready access for in-migration of epithelial cells, as at panel (c) indicated by arrows I. The second layer is directly adhered to eye 200 at a plurality of locations 206 so that its position is retained on eye 202 while the in-migration takes place. The upper layer ultimately degrades and locations wherein the upper layer is attached directly to the eye heal. FIG. 6B depicts this embodiment in partial elevated cross-section. At panel (a), area 202 is partially covered with a masking layer 204 that leaves tie points 206 on area 202. At panel (b), a second layer, overlayer 208, is applies. At panel (c), the masking layer has disintegrated and epithelial cells have replaced the same 220. At panel (d), re-epithelialization is complete.

The first layer and second layers may be prepared as described herein, with the relative biodegradation rates being controlled, as described herein with respect to biodegradable materials and/or precursors. One of these options relates to choosing among hydrolytically degradable precursors with succinimidyl groups, with a choice of groups known to degrade at different rates as a result of exposure to water. Thus, for instance, the first layer may comprise a hydrogel with succinimidyl groups that hydrolytically degrade more quickly relative to the second layer. One or both of the layers may consist of, or be comprised of, a biocompatible, bioresorbable, or dissolvable material that forms a coating, e.g., a covalently cross-linked hydrogel, a hydrogel comprised of non-covalent crosslinks, a thixotropic solution, hyaluronate, hydroxymethylproplycellulose, PLURONICs, a polysaccharide, a protein, or a combination thereof.

One embodiment of the first layer, also referred to herein as a masking layer, is a compressed biodegradable material. The material may be dry, partially hydrated, or fully hydrated before application. For instance, hyaluronic acid or other materials may be compressed (or stamped, or molded) into a thin mask that has the plurality of openings. A user places the mask over the zone, and subsequently applies an overlayer. For instance, a pharmaceutically acceptable grade of gelatin may be stamped into a mask with a plurality of openings that will provide the tie points. The gelatin may be free of covalent crosslinks. The gelatin may be dry-stamped or fully or partially solvated before compression. Similarly, other degradable materials, or materials that are water soluble may be prepared. Further examples are polysaccharides (e.g., alginate, xanthan gum, carrageenan) or proteins (albumin, gelatin).

As an example, the first layer may be provided with a degradation rate of about 0.5 to about 5 days; artisans will immediately appreciate that all the ranges and values within the explicitly stated ranges are contemplated, e.g., in no more than about 1 day, no more than about 2 days, or between 0.5 and 3 days. Further, the second layer may be provided with a degradation time of between, for instance, about 1 and about 14 days; artisans will immediately appreciate that all the ranges and values within the explicitly stated ranges are contemplated, e.g, about 4 days, about 8 days, or in a range of about 4 to about 10 days. The second layer may be provided with a degradation time that is relatively greater than the first payer, e.g., between about 1 and about 10 days greater; artisans will immediately appreciate that all the ranges and values within the explicitly stated ranges are contemplated.

The loci that are free of the first layer and in contact with the second (upper) layer can be prepared in a variety of ways. A first technique is to apply the first layer with a hand-held applicator configured to apply small volumes (brush, sponge, soft-tip) of material, e.g., a thixotropic solution or hydrogel precursors.

Another technique is to pre-form the first layer (a "mask") and apply it to the eye. The pre-formed layer may be formed of materials described herein, e.g., hydrogels, PEG hydrogels, hydrolytically degradable materials, biodegradable materials. The pre-formed layer comprises a plurality of openings and is placed on the wounded area. The pre-formed layer may be sized to essentially match the wound area without extending beyond it, or may be substantially larger than the wound area.

EXAMPLES

PEG is an acronym for polyethylene glycol or polyethylene oxide, a polymer with —($CH_2CH_2O$)— repeats. Molecular weights are abbreviated in thousands, e.g., with 15K meaning 15,000 molecular weight, i.e., 15,000 Daltons. SG refers to succinimidyl glutarate. SS refers to succinate succinimide. SS and SG are succinimidyl esters that have an ester group that degrades by hydrolysis in water. Hydrolytically degradable thus refers to a material that would spontaneously degrade in vitro in an excess of water without any enzymes or cells present to mediate the degradation. Trilysine (also abbreviated LLL) is a synthetic tripeptide. Water for injection (WFI) refers to water used to make-up solutions that are intended to be placed in a patient; this water is pharmaceutically acceptable, meaning that it is highly purified and free of contaminants, e.g., pyrogens. Animal models were rabbits, which are conventionally accepted as sensitive and suitable models for human treatments.

The hydrogel solutions were prepared by making dried deposits in an elongated well of a polycarbonate tray (FIG. 5). Gels were prepared by adding water for injection (WFI) to each deposit, then mixing the two together with a rod. The gels were then applied with a nonabsorbent brush-tipped applicator that a user could manipulate to pick up between about 1 µl to about 100 µl considering the size of the brush and the depth and angle of placement into the mixed drops. The dilution of the mixture of the drops was varied as described. Solids content is reported as the w/w content of the precursors compared to total weight of precursors and water.

Example 1

Test Conditions, Hydrogel Swelling (Shrinkage) and Degradation for Hydrogels

One deposit consisted of 8 arm 15K SG PEG (8.7 mg), sodium phosphate monobasic buffer, and FD&C Blue #1 (0.01 mg). The other deposit consisted of trilysine acetate (0.52 mg), sodium phosphate dibasic and sodium tetraborate decahydrate. Water volumes were varied with WFI from 40 µl to 280 µl in 40 µl increments to provide a range of gels with varied solids content. The succinimidyl glutarate:amine ratio was 1:1. Degradation In Vitro Phosphate Buffered Saline (PBS) was added to vials containing the gels. The vials were then transferred to a 37° C. water bath for degradation. The degradation process as tracked by daily visual inspection until complete disappearance of the sample was observed.

Gel Time Testing

Gel time was tested using a polycarbonate rod (2 inch long and one-eighth inch diameter) to stir the two solutions within the tray well and then lifting the rod 3 inches every second. Gel time ("gelation") was defined as the time (by stopwatch) required until a strand formed spanning the 3 inches from the solution to the rod.

Animal Testing

The epithelium of rabbit eyes were removed to form a circular area on the cornea of 8 mm in diameter. The removal of the epithelium was accomplished by applying a stainless steel tube (8 mm ID) to the corneal surface and placing a 20% ethanol/water solution in the tube for 30 seconds. The epithelium was then easily removed with a WECK CELL swab. The sample solution was then applied with a limn nylon brush and allowed to gel. The gel was allowed to set for 1 minute before irrigation. The eyes were treated with an antibiotic solution (VIGAMOX) and a steroid (PRED FORT). The eyes were observed daily until the material degraded (disappeared), or the study was terminated.

Series 1 was tested for the effect of dilution with water for injection (WFI) on gel time and swelling behavior. The results of this testing are shown in Table 1. The gel time lengthened with dilution due to the reduction of reactant concentrations.

TABLE 1

Results for series 1 hydrogels

| Sample | WFI (µL) | Solids (%) | Gel Time (s) | Swelling (%) |
|---|---|---|---|---|
| 1 | 40 | 20.4 | 9 | 53 |
| 2 | 80 | 10.2 | 25 | 6 |
| 3 | 120 | 6.8 | 55 | −3 |
| 4 | 160 | 5.1 | 106 | −10 |
| 5 | 200 | 4.08 | 221 | 40 |
| 6 | 240 | 3.4 | 397 | 40 |
| 7 | 280 | 2.9 | 607 | 33 |

A rabbit study was used to explore the persistence time of the diluted gel for this application. The series 1 material diluted with 160 ul WFI (5.1% solids) was applied to the corneal surface after removal of the epithelium. Examination of the animals showed no major difference between treated and control eyes after 24 hours. The second check up at day 5 showed complete healing of the control eye and minor healing in the treated eye. At day 15 the bandage seemed to be persistent on the treated eye with a crescent shape which was believed to be the effect of the mechanical movement of the nictitating (third) eyelid. Although this material was diluted such that gel time was greater than 1 minute, the persistence was greater than fifteen days.

Example 2

Hydrogel Swelling (Shrinkage) and Degradation for Alternative Hydrogels

The materials and methods of Example 1 were used except that a buffered diluent was used instead of WFI to make the solution in order to minimize the effect of diluent on the gel time of the composition. For that reason, both sodium phosphate dibasic and sodium tetraborate decahydrate salts were changed from being dried deposits in Example 1 to being dissolved in solution with water for injection to make the diluent in Example 2. Gels were prepared by adding diluent to each deposit, then mixing the two together. Diluent volumes were varied from 160 µl to 320 µl in 40 µl increments to provide a range of gels with varied solids content. The results are shown in Table 2.

This formulation was diluted with a diluent rather than water as in the Series 1 formulation. Since the diluent contained sodium phosphate dibasic and sodium tetraborate decahydrate, it was basic in pH additional diluent resulted in less gel time lengthening than in Series 1. It was found that although the material was diluted to as little as 2.6% solids, which is an extremely weak material mechanically, degradation time was not decreased enough to match the healing time of the epithelium (about one week). In a previous study, a dilution of 80 µl, of another lot of this formulation disappeared at 57 days, which is consistent with the trend of these more diluted samples.

TABLE 2

The effect of dilution on gel time and degradation for Series 2

| Sample | Diluent (μL) | Solids (%) | Gel Time (s) | Disappearance (days) |
|---|---|---|---|---|
| 1 | 160 | 5.1 | 26.5 | 51 |
| 2 | 160 | 5.1 | 25.0 | 51 |
| 3 | 200 | 4.1 | 31.8 | 48 |
| 4 | 200 | 4.1 | 30.9 | 48 |
| 5 | 240 | 3.4 | 37.3 | 40 |
| 6 | 240 | 3.4 | 35.6 | 40 |
| 7 | 280 | 2.9 | 47.6 | 33 |
| 8 | 280 | 2.9 | 43.2 | 33 |
| 9 | 320 | 2.6 | 60.7 | 30 |
| 10 | 320 | 2.6 | 57.1 | 30 |

Example 3

Hydrogel Swelling (Shrinkage) and Degradation for Alternative Hydrogels

Another alternative hydrogel formulation, series 3, was tested as in Example 2. The formulation used in series 3 was essentially identical to that used in Example 2, with the exception of the polyethylene glycol (PEG) macromer. In series 3, the macromer end groups were changed from glutarate (SG) to succinate (SS). The base polymer was an 8 arm 15K PEG SS molecule. The results of this testing are shown in Table 3.

As in Example 2, the effect of dilution is smaller than in Example 1. In fact, Example 3 showed no effect of dilution over the range studied. It should be noted that a Example 2 formulation at a dilution of 80 μl, typically gels in 25 seconds. The Example 2 material in Table 3 shows that at 160 μl dilution the gel time is still about 25 seconds, which agrees with the results for Example 3 in Table 3.

TABLE 3

The effect of dilution on gel time and degradation for Series 3

| Sample | Diluent (μL) | Solids (%) | Gel Time (s) | Disappearance (days) |
|---|---|---|---|---|
| 1 | 80 | 10.2 | 27.0 | 4 |
| 2 | 80 | 10.2 | 27.4 | 4 |
| 3 | 120 | 6.8 | 26.7 | 3-4 |
| 4 | 120 | 6.8 | 27.1 | 3-4 |
| 5 | 160 | 5.1 | 25.6 | 3 |
| 6 | 160 | 5.1 | 25.6 | 3 |

Example 4

Healing Rate of Hydrogel Treated De-Epithelialized Corneal Zones

Experiments were preformed as in Example 1, with changes or further detail as follows. All animals had daily clinical exams for general health. In addition the surgical sites were examined daily for normal healing and infection (wound healing observations). All animals were observed for gel retention via observations using fluorescein staining and measurement of the stained dimensions (gel retention observations). All animals were observed for re-growth of their epithelial layer using visual microscopy with UV exposure and fluorescein staining techniques (epithelium regrowth). Histological evaluation was done to assess wound healing and inflammatory cell infiltration to the wound site. Under general anesthesia, de-epithelialization was performed on both eyes. The left eye was used as the control eye. The right eye was treated with hydrogel. All animals (n=10) (White New Zealand rabbits) received 1 drop of ZYMAR (gatifloxacin ophthalmic solution 0.3%) in both eyes daily. All eyes also received 2 drops of PRED FORTE 1% (Postsurgical) since the third eyelids were removed during the procedure. Inflammation in the eyes were ranked as the following: Severe Inflammation: SI, Mild Inflammation: MI, No Inflammation: NI. Two animals were humanely euthanized at every time point. The corneas were processed for evaluation of corneal cross sections. Initial staining was H&E.

In this Example the formulation consisted of two dried deposits in an elongated well of a polycarbonate tray. One deposit consisted of 8 arm 15K SS PEG (8.2 mg) and sodium phosphate monobasic (0.04 mg). The other deposit consisted of trilysine acetate (0.52 mg) and FD&C Blue #1 (0.01 mg). A diluent solution was prepared containing sodium phosphate dibasic (364.2 mg) and sodium tetraborate decahydrate (214.4 mg) and water for injection (50 g). Gels were prepared by adding 40 mg of diluent to each deposit, then mixing the two together, with about 10.2% solids content (Table 3).

Based on the dimensions of the fluorescein stained area caused by the gel in treated eyes or by injured tissue in control eyes, the wound area was determined and averaged for each time point. The average reduction of wound area percent over time was calculated as shown in Table 4 and plotted in FIG. 2. Some severe cases of inflammation were observed at day 1 due to the removal of the third eye lids during the procedure at day 0. Mild cases of inflammation were observed past day 2. No signs of inflammation were observed past day 3.

TABLE 4

Reduction of wound area over time

| | Average Percent of Initial Wound Area | |
|---|---|---|
| Days | Control | Treated |
| 0 | 100 | 100 |
| 1 | 54 | 74 |
| 2 | 19 | 40 |
| 3 | 10 | 13 |
| 5 | 0 | 0.4 |
| 7 | 0 | 0 |

Corneas were collected at different time points and processed for histology. FIG. 3 shows cross sections of dissected corneas at day 1. FIG. 3 panel (a) shows a complete de-epithelialization of the corneal surface in a control eye. FIG. 3 panel (b) shows a junction between the epithelialized and the gel treated corneal surface. It is typical for hydrogels to be damaged by the process used to prepare the histology slides; therefore, these micrographs should not be interpreted to represent the gel appearance in vivo. FIG. 3 panel (c) shows the de-epithelialized corneal surface treated with a continuous adherent gel coating. Arrowheads mark the transition from epithelialized tissue to non-epithelialized tissue.

This experiment demonstrated that the gel met those efficacy targets and performed well in this animal model. The hydrogel material was applied on the de-epithelialized corneal surface. The gel showed persistence throughout the healing period. The eyes were essentially healed by day 5, with confirmation of complete healing on day 7.

It should be noted that the persistence of the Ocular Bandage did not interfere with the healing process in the treated eyes when compared to the untreated control eyes past day 3, where the percentage of initial wound area results for control and treated eyes converged.

These results indicated there were no significant differences in the histological appearance of the control and treated eyes at any time point. Analysis of all corneas showed no signs of any inflammatory cell infiltration into the injured area. Minimal edema was noted in all samples with no difference noted between control and treated eyes.

A second experiment (not detailed herein) was conducted in which neither treated nor control eyes received anti-inflammatory drugs. Even without the anti-inflammatory drugs, minimal inflammation was noted in control and treated eyes.

Additional experiments were performed with the same essential conditions, with the solids content being 7.5% or 5%. Histological evaluation of the samples (n=8) indicated reduced edema compared to control samples (n=4). Further, at day 7, 2 of the 4 control samples showed incomplete re-epithelialization but only 1 of 8 treated samples showed the same.

Example 5

Healing Rate of Hydrogel Treated De-Epithelialized Corneal Zones Made by Mechanical Ablation This Example was performed as in Example 4, with changes noted as follows. De-epithelialization was performed using an Amoils brush to create a 9 mm diameter area. Following this the Amoils brush was modified with an abrasive material and the de-epithelialize surface was abraded for 10 seconds with firm pressure. The gel was as in Example 4, except that more diluent (120 mg) was used to reduce the concentration to about 6.8% solids. It was applied the same way as in Example 4, keeping the gel substantially in the defect area.

Figure 7:
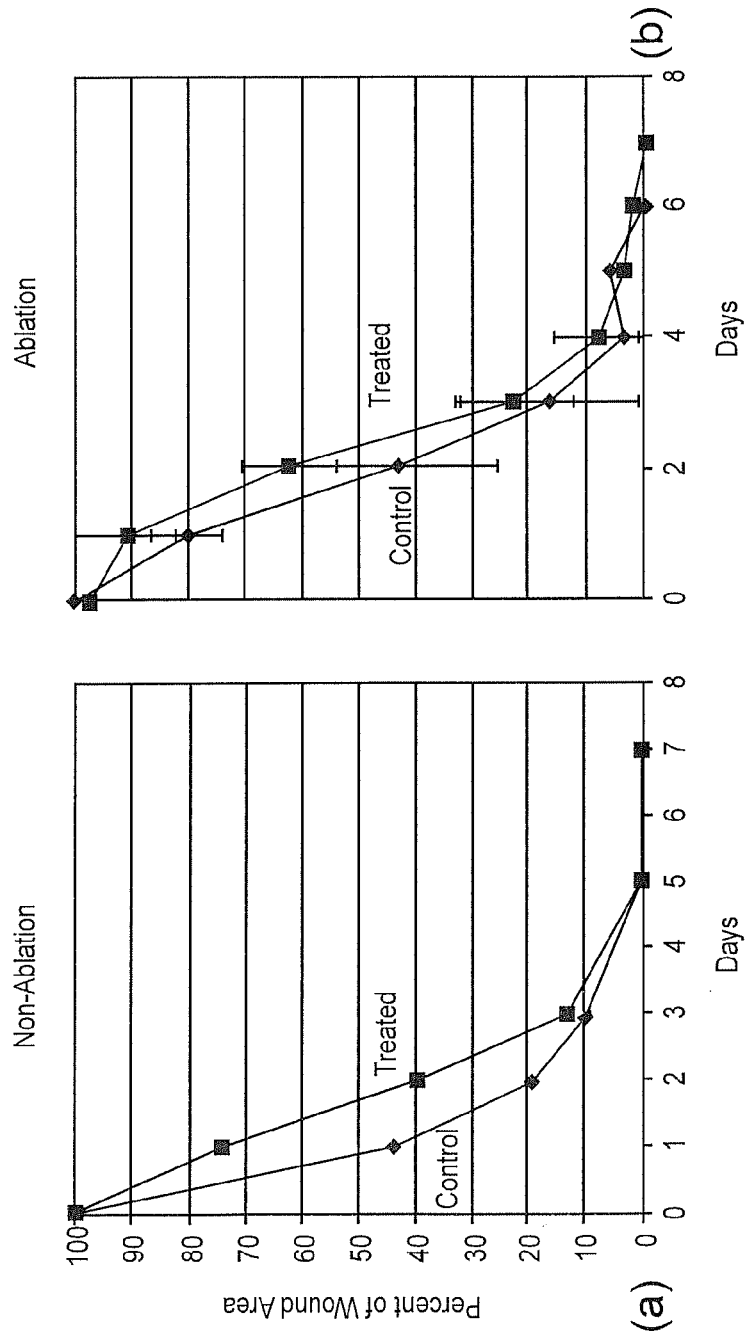
FIG. 7 depicts the results of FIG. 2 in panel (a) and at panel (b) is a plot of healing of an ablation defect with a hydrogel-treatment as compared to an untreated control eye.

FIG. 7 is a graph of the results. Panel (a) depicts the results shown in FIG. 2 for coated and non-coated defect areas that had only de-epithelialization and no ablation. Panel (b) depicts defect areas created by ablation and coated with the gels as compared to controls with no gels. Healing of coated defect areas was comparable to healing with uncoated areas.
Further Description A method of treating a de-epithelialized zone on a corneal surface of an eye comprising applying a volume of a solution of a hydrogel precursor in the zone on the eye, with the precursor crosslinking to form a covalently crosslinked degradable hydrogel. A composition and/or use of a hydrogel for treating a corneal surface of an eye comprising a volume of a hydrogel (and/or an aqueous solution of a hydrogel precursor that forms a hydrogel). A kit, system and/or process for treating an eye comprising components to prepare a volume of a flowable aqueous solution of hydrogel precursors that has a pH of between about 6 and about 8, with the precursors spontaneously crosslinking to form a covalently crosslinked hydrolytically degradable hydrogel. A method of, a use of, and a composition for, reducing pain following photorefractive keratectomy that creates a de-epithelialized zone on a corneal surface comprising applying a volume of a flowable aqueous solution of a hydrogel precursor in the zone on the eye, with the precursor spontaneously crosslinking to form a crosslinked hydrogel. A kit of medical hydrogel components in a single housing that comprises a well (or a flat surface, or a surface, with the same being applicable to other embodiments using a well, a first hydrogel precursor in a dry form immobilized in a first deposit at a first location in the well, a second hydrogel precursor in a dry form immobilized in a second deposit at a second location in the well, water or an aqueous solution, and an applicator. A method of, a use of, and a composition for, treating a patient by application of a hydrogel bandage to an eye comprising providing a first hydrogel precursor in a dry form immobilized in a first deposit at a first location mixing the deposit to form a mixture, and transferring a volume of the mixture to the eye, with the mixture forming a crosslinked hydrogel.

A method of treating a de-epithelialized zone on a corneal surface of an eye and having a depth of about 10 to about 200 μm comprising applying a volume of a flowable aqueous solution of a hydrogel precursor in the zone on the eye and filling the zone without spreading the solution substantially outside the zone to keep the solution substantially only within the zone, with the precursor spontaneously crosslinking to form a covalently crosslinked hydrolytically degradable hydrogel that fills the de-epithelialized zone without extending substantially outside the zone and that has a height that is not more than about 200 μm above eye tissue adjacent to the de-epithelialized zone.

A composition and/or use of a hydrogel for treating a de-epithelialized zone on a corneal surface of an eye having a depth of about 10 to about 200 μm comprising (applying) a volume of a flowable aqueous solution of a hydrogel precursor in the zone on the eye that fills the zone without spreading the solution substantially outside the zone to keep the solution substantially only within the zone, with the precursor spontaneously crosslinking to form a covalently crosslinked hydrolytically degradable hydrogel that fills the de-epithelialized zone while remaining substantially only within the zone and that has a height that is not more than about 200 μm above eye tissue adjacent to the de-epithelialized zone.

A kit, system and/or process for treating a zone on a corneal surface of an eye and having a depth of about 10 to about 200 μm comprising a volume of a flowable aqueous solution of hydrogel precursors that has a pH of between about 6 and about 8, with the precursors spontaneously crosslinking to form a covalently crosslinked hydrolytically degradable hydrogel that has a solids content of between about 3% and about 15% w/w, wherein the hydrogel is fully degraded in vitro in aqueous physiological saline within no more than about 10 days after initial formation, wherein the precursors comprise a first precursor that comprises a succinimidyl ester functional group and a second precursor that comprises a second functional group, with the succinimidyl ester functional group and the second functional group reacting with each other to form covalent bonds to thereby form the covalently crosslinked hydrogel within about 10 to about 100 seconds of bringing the first and second precursors together in the solution, with one of the precursors comprising a hydrophilic polymer with a molecular weight of at least about 3,000 and the other precursor having a molecular weight of less than about 1,000, wherein, over a predetermined period of about 1 or 2 or 3 or 4 days beginning at formation of the hydrogel, disappearance of the hydrogel on a surface of an eye progresses from outer edges of the hydrogel to the center of the hydrogel, with remaining persistent portions of the hydrogel blocking migration of epithelial cells. May include an applicator comprising a delivery surface sized to pick up no more than about 1 to about 100 μl of the volume and transfer the solution to a surface of an eye.

A method of, a use of, and a composition for, reducing pain following photorefractive keratectomy that creates a de-epithelialized zone on a corneal surface comprising applying a volume of a flowable aqueous solution of a hydrogel precursor in the zone on the eye and filling the zone without spreading the solution substantially outside the zone to keep the solution substantially only within the zone, with the precursor spontaneously crosslinking to form a covalently crosslinked hydrolytically degradable hydrogel that fills the de-epithelialized zone (without extending substantially outside the zone) and that has a height that is not more than about 200 µm above eye tissue adjacent to the de-epithelialized zone, with the hydrogel providing for re-epithelialization of the cornea in a period of days that is no more than a period of days for a eye that undergoes the same treatment but does not receive the hydrogel.

A kit of medical hydrogel components in a single housing that comprises a tray comprising a well, a first hydrogel precursor in a dry form immobilized in a first deposit at a first location in the well, a second hydrogel precursor in a dry form immobilized in a second deposit at a second location in the well, water or an aqueous solution in a dropper, a mixing rod, and an applicator comprising a delivery surface sized to hold a volume of no more than about 100 µl of a liquid volume and proportioned for manual transfer of the volume to a surface of an eye; wherein the first precursor comprises first functional groups and the second precursor comprises second functional groups, with the first and the second functional groups chemically reacting with each other to form covalent bonds to thereby crosslink the precursors into a hydrogel.

A method of, a use of, and a composition for, treating a patient by application of a hydrogel bandage to a cornea comprising providing a first hydrogel precursor in a dry form immobilized in a first deposit at a first location in a well, providing a second hydrogel precursor in a dry form immobilized in a second deposit at a second location in the well, adding less than 1000 µl of aqueous solution to one or more of the deposits; mixing the deposits together with a mixing rod to form a mixture, introducing a delivery surface to the mixture and recovering a volume between about 1 and about 100 µl of the mixture, transferring at between 1 and 100 µl of the volume from the delivery surface to the cornea, with the mixture forming a covalently crosslinked hydrogel on the cornea.

A kit and/or a method of treating a de-epithelialized zone on a corneal surface of an eye comprising applying a first masking layer comprising a degradable material to the zone on the eye, with a plurality of tie point locations in the zone being free of contact with the first layer, applying a volume of a flowable aqueous solution of a hydrogel precursor over the first layer, with the precursor spontaneously crosslinking to form a covalently crosslinked hydrolytically degradable hydrogel to thereby form a second layer that contacts the first layer and adheres to the zone at the plurality of tie point locations. A coating for an eye, the coating comprising a first masking layer on the eye and a second layer at least partially covering the masking layer, with the masking layer comprising a plurality of openings that are filled by the second layer, which contacts the eye at the openings, wherein the masking layer degrades more rapidly than the second layer. The kit, coating, and/or method wherein the first masking layer is a covalently crosslinked hydrogel adherent to the zone, wherein the first layer and the second layer are hydrolytically degradable and with the first layer being degradable more quickly than the second layer. The kit, coating, and/or method wherein the first layer is applied as an aqueous solution that comprises a hydrogel precursor that is covalently crosslinked to form at least a part of the hydrogel of the first layer. The kit, coating and/or method wherein the first layer is a covalently crosslinked hydrogel formed prior to application to the zone, with the first layer comprising a plurality of openings that provide the tie point locations. The kit, coating, and/or method wherein the first and/or second layer further comprises a visualization agent for visualizing one or more of the layers. A pre-formed masking layer comprising a plurality of openings, with the openings providing tiepoints for a subsequently applied overlayer that is adherent to the eye; a kit comprising the pre-formed layer and materials for the second layer, and applicators, with instructions. The pre-formed layer may comprise a covalently crosslinked hydrogel or other hydrogel, including xerogels. The first masking layer may comprise a solid material formed prior to application to the zone, with the first layer further comprising a plurality of openings that provide the tie point locations. For example, the solid material may comprises PEG (pure PEG, a PEG copolymer), a polysaccharide, a protein, or a combination thereof.

Materials and Methods as above, wherein the hydrogel is fully degraded on the surface within less than about 10 days. Further embodiments provide that, over a period of about 2 days beginning at the application of the hydrogel, disappearance of the hydrogel progresses from outer edges of the zone to the center of the zone, with migrating epithelial cells being continuously adjacent the hydrogel without being substantially under the hydrogel. The methods and compositions may further comprise creating a de-epithelialized zone by surgically removing tissue from the surface of the eye, e.g., by laser, PRK, or mechanical means. The volume may be predetermined and chosen to be between 1 and 100 µl, with precursor solutions being manually spread with an applicator to achieve coverage of the desired area, e.g., a de-epithelialized zone without extension of the solution and the resultantly formed hydrogel substantially outside of the zone. The solution placed on the eye with the precursors may be provided with a pH of between about 6 and about 8. A first precursor may comprise a first functional group and the precursor solution may further comprise a second precursor with a second functional group, with the first functional group and the second functional group reacting with each other to form covalent bonds to thereby form the covalently crosslinked hydrogel. Embodiments include such materials or methods wherein the first precursor may comprise polyethylene glycol and the first functional group or the second functional group may comprise a succinimidyl ester, e.g., SS or SG. The hydrogel embodiments include hydrogels with a solids content of between about 3% and about 15% w/w. A precursor solution may be made that further comprises a visualization agent that, before application to the eye, is visible without a machine aid to a user applying the solution. The visualization agent may be placed in one or more depots of precursors. An applicator may be provided with a first and second end, with the mixing rod forming the first end and the delivery surface being on the second end. A therapeutic agent may be delivered from a hydrogel.

Various embodiments have been described that exemplify the invention. These embodiments have features that, in general, may be mixed and matched as needed.

The invention claimed is:

1. A method of treating a patient by application of a hydrogel bandage to a cornea comprising:
providing a first hydrogel precursor in a dry form immobilized in a first deposit at a first location in a well,
providing a second hydrogel precursor in a dry form immobilized in a second deposit at a second location in the well,
adding less than 1000 µl of aqueous solution to one or more of the deposits to thereby dissolve the first and/or the second hydrogel precursor;
mixing the deposits together to form a mixture comprising the first hydrogel precursor and the second hydrogel precursor, introducing a delivery surface to the mixture and recovering a volume between 1 and 100 µl of the mixture transferring at between 1 and 100 µl of the volume from the delivery surface to the cornea, with the mixture forming a covalently crosslinked hydrogel on the cornea, wherein said immobilization prevents the hydrogel precursor from moving from the location until such time as it is dissolved in the aqueous solution and wherein said immobilization prevents the first hydrogel precursor in the dry form and the second hydrogel precursor in the dry form from mixing together before being dissolved.

2. The method of claim 1 wherein the first precursor comprises a first functional group and the second precursor comprises a second functional group, with the first functional group and the second functional group reacting with each other to form covalent bonds to thereby form the covalently crosslinked hydrogel.

3. The method of claim 1 wherein the first and/or second deposit further comprises a visualization agent that, before application to the eye, is visible without a machine aid to a user applying the solution.

4. The method of claim 1 wherein the hydrogel is fully degraded on the cornea within less than 10 days.

5. The method of claim 1 wherein the mixture has a pH of between 6 and 8.

6. The method of claim 2 wherein the first precursor comprises polyethylene glycol and the first functional group or the second functional group comprises a succinimidyl ester.

7. The method of claim 2 with the mixture further comprising a drug subsequently released from the hydrogel.

8. The method of claim 1 wherein the covalently crosslinked hydrogel has a solids content of between 3% and 15% w/w.

9. The method of claim 1 wherein the mixture further comprises a visualization agent that, before application to the eye, is visible without a machine aid to a user applying the mixture.

10. The method of claim 1 wherein the mixture further comprises a drug subsequently released from the covalently crosslinked hydrogel.

11. The method of claim 1 wherein the deposits are mixed using an applicator comprises a first and second end, with a mixing rod forming the first end and the delivery surface being on the second end.

* * * * *